(12) United States Patent
Walter et al.

(10) Patent No.: US 12,420,096 B2
(45) Date of Patent: Sep. 23, 2025

(54) ELECTRODE ARRAYS AND COCHLEAR IMPLANTS INCLUDING THE SAME

(71) Applicant: ADVANCED BIONICS AG, Staefa (CH)

(72) Inventors: Jeryle L. Walter, Valencia, CA (US); James George Elcoate Smith, Santa Clarita, CA (US); Uli Gommel, Valencia, CA (US); Matthew Vadim Krywcun, Saugus, CA (US); Sarah Elizabeth Clabeaux, Ventura, CA (US); Nicholas Anthony Wise, Pasadena, CA (US); Sung Jin Lee, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 1097 days.

(21) Appl. No.: 17/383,867

(22) Filed: Jul. 23, 2021

(65) Prior Publication Data
US 2021/0353944 A1 Nov. 18, 2021

Related U.S. Application Data

(63) Continuation of application No. 16/406,721, filed on May 8, 2019, now Pat. No. 11,103,704, which is a continuation-in-part of application No. PCT/US2017/060030, filed on Nov. 3, 2017.

(60) Provisional application No. 62/419,349, filed on Nov. 8, 2016.

(51) Int. Cl.
*A61N 1/36* (2006.01)
*A61N 1/05* (2006.01)
*A61N 1/372* (2006.01)

(52) U.S. Cl.
CPC ....... *A61N 1/36038* (2017.08); *A61N 1/0541* (2013.01); *A61N 1/37229* (2013.01)

(58) Field of Classification Search
CPC .............. A61N 1/36038; A61N 1/0541; A61N 1/37229
See application file for complete search history.

(56) References Cited

U.S. PATENT DOCUMENTS

| | | | |
|---|---|---|---|
| 5,123,422 A | 6/1992 | Charvin | |
| 5,454,795 A * | 10/1995 | Samson | .............. C08L 79/08 |
| | | | 604/526 |
| 5,702,373 A | 12/1997 | Samson | |

(Continued)

FOREIGN PATENT DOCUMENTS

| | | |
|---|---|---|
| CN | 101889910 A | 11/2010 |
| CN | 102958562 A | 3/2013 |

(Continued)

OTHER PUBLICATIONS

U.S. Appl. No. 16/463,957, filed May 24, 2019.

(Continued)

*Primary Examiner* — Lindsey G Wehrheim
(74) *Attorney, Agent, or Firm* — Henricks Slavin LLP

(57) ABSTRACT

A cochlear including a housing, an antenna, a stimulation processor operably connected to the antenna, and an electrode array, operably connected to the stimulation processor, including a flexible body defining a longitudinal axis, a proximal region and a distal region, a plurality of electrically conductive contacts on the flexible body, and at least one stiffener within the flexible body.

16 Claims, 15 Drawing Sheets

(56) References Cited

U.S. PATENT DOCUMENTS

| | | | |
|---|---|---|---|
| 6,048,338 A * | 4/2000 | Larson | A61M 25/0054 604/525 |
| 6,119,044 A | 9/2000 | Kuzma | |
| 6,144,883 A | 11/2000 | Kuzma | |
| 6,421,569 B1 | 7/2002 | Treaba et al. | |
| 6,541,014 B2 | 4/2003 | Rudnic et al. | |
| 7,881,811 B2 | 2/2011 | Risi | |
| 8,249,724 B2 | 8/2012 | Risi et al. | |
| 8,812,121 B2 | 8/2014 | Risi et al. | |
| 8,868,213 B2 | 10/2014 | Shan et al. | |
| 8,880,187 B2 | 11/2014 | McDonald et al. | |
| 8,880,193 B1 | 11/2014 | Thenuwara et al. | |
| 9,033,869 B2 | 5/2015 | Thenuwara et al. | |
| 9,037,267 B2 | 5/2015 | Thenuwara et al. | |
| 9,050,457 B2 | 6/2015 | Foster et al. | |
| 9,211,403 B2 | 12/2015 | Tortonese et al. | |
| 9,415,207 B2 | 8/2016 | Thenuwara et al. | |
| 9,492,654 B2 | 11/2016 | Thenuwara et al. | |
| 9,937,345 B2 | 4/2018 | Knisely et al. | |
| 10,994,138 B2 | 5/2021 | Walter et al. | |
| 11,103,704 B2 | 8/2021 | Walter et al. | |
| 11,123,551 B2 | 9/2021 | Hoffman et al. | |
| 12,036,402 B2 | 7/2024 | Hoffman et al. | |
| 2002/0029074 A1 | 3/2002 | Treaba et al. | |
| 2003/0032997 A1 | 2/2003 | Pianca et al. | |
| 2007/0135884 A1 | 6/2007 | Risi | |
| 2008/0004684 A1 | 1/2008 | Dadd et al. | |
| 2009/0030483 A1 | 1/2009 | Risi et al. | |
| 2010/0204768 A1 | 8/2010 | Jolly et al. | |
| 2010/0318167 A1 | 12/2010 | Conn et al. | |
| 2011/0016710 A1 | 1/2011 | Dadd et al. | |
| 2011/0071596 A1 | 3/2011 | Kara et al. | |
| 2011/0137393 A1 | 6/2011 | Pawsey et al. | |
| 2011/0144733 A1 | 6/2011 | Dadd et al. | |
| 2011/0264183 A1 | 10/2011 | Gibson et al. | |
| 2011/0295352 A1 | 12/2011 | Thenuwara et al. | |
| 2012/0221088 A1 | 8/2012 | Thenuwara et al. | |
| 2013/0090711 A1 | 4/2013 | Ramachandran et al. | |
| 2013/0245740 A1 | 9/2013 | Ramachandran et al. | |
| 2014/0005599 A1 | 1/2014 | Sage et al. | |
| 2014/0094892 A1 | 4/2014 | Thenuwara et al. | |
| 2014/0163662 A1 | 6/2014 | Beerling et al. | |
| 2014/0277275 A1 | 9/2014 | Djunaedi et al. | |
| 2015/0119967 A1 * | 4/2015 | Pawsey | A61N 1/0541 607/137 |
| 2016/0015965 A1 | 1/2016 | Leavens | |
| 2016/0022990 A1 | 1/2016 | Risi | |
| 2017/0056646 A1 * | 3/2017 | Sibary | A61N 1/0541 |
| 2018/0200517 A1 | 7/2018 | Knisely et al. | |
| 2019/0275325 A1 | 9/2019 | Walter et al. | |
| 2019/0329028 A1 | 10/2019 | Walter et al. | |
| 2020/0384262 A1 | 12/2020 | Hoffman et al. | |
| 2021/0379365 A1 | 12/2021 | Hoffman et al. | |
| 2024/0325732 A1 | 10/2024 | Hoffman et al. | |

FOREIGN PATENT DOCUMENTS

| | | |
|---|---|---|
| CN | 104644330 A | 5/2015 |
| EP | 1189560 A1 | 3/2002 |
| EP | 2303397 B1 | 4/2014 |
| WO | WO 96/31087 A1 | 10/1996 |
| WO | WO 00/71063 A1 | 11/2000 |
| WO | WO 2007/027879 A1 | 3/2007 |
| WO | WO 2009/065127 A1 | 5/2009 |
| WO | WO 2009/079704 A1 | 7/2009 |
| WO | WO 2012/003295 A1 | 1/2012 |
| WO | WO 2015/030734 A1 | 3/2015 |
| WO | WO 2018/031025 A2 | 2/2018 |
| WO | WO 2018/089272 A1 | 5/2018 |
| WO | WO 2018/102695 A2 | 6/2018 |

OTHER PUBLICATIONS

U.S. Appl. No. 16/343,496, filed Apr. 19, 2019.
U.S. Appl. No. 16/406,721, filed May 8, 2019.
PCT International Search and Written Opinion dated Jan. 24, 2018 for PCT App. Ser. No. PCT/US2017/060030.
U.S. Appl. No. 17/407,350, filed Aug. 20, 2021.
U.S. Appl. No. 17/383,867, filed Jul. 23, 2021.
U.S. Appl. No. 17/407,350, filed Aug. 20, 2021, 2021/0379365 A1.
U.S. Appl. No. 16/463,957, filed May 24, 2019, 11123551 B2.
U.S. Appl. No. 17/407,350, filed Aug. 20, 2021, 12036402 B2.
U.S. Appl. No. 18/739,759, filed Jun. 11, 2024, 20240325732 A1.
U.S. Appl. No. 16/343,496, filed Apr. 19, 2019, 10994138 B2.
U.S. Appl. No. 16/406,721, filed May 8, 2019, 11103704 B2.
U.S. Appl. No. 17/383,867, filed Jul. 23, 2021, 20210353944 A1.

* cited by examiner

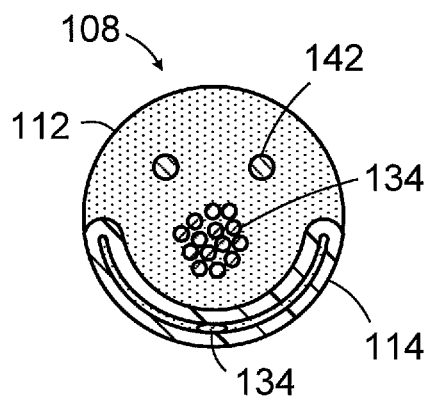
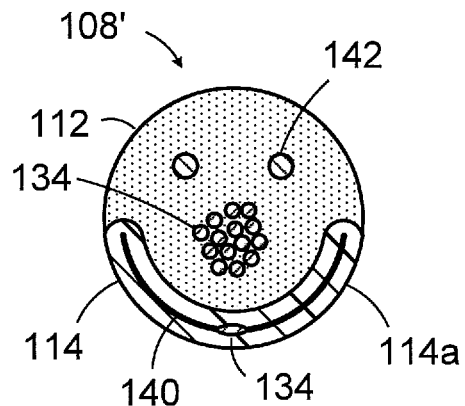
FIG. 6     FIG. 7
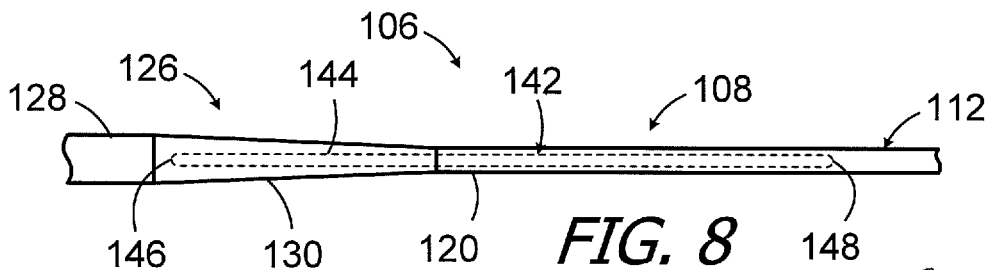
FIG. 8
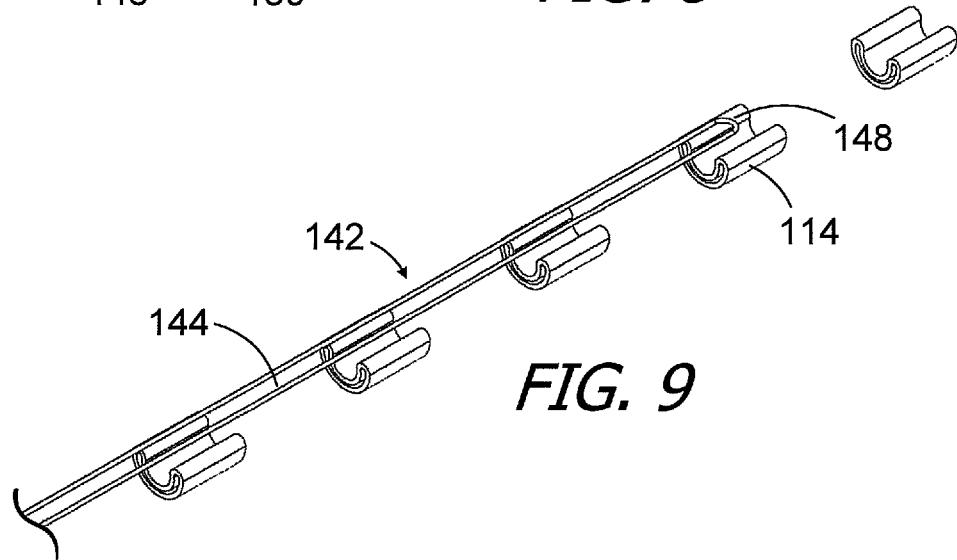
FIG. 9
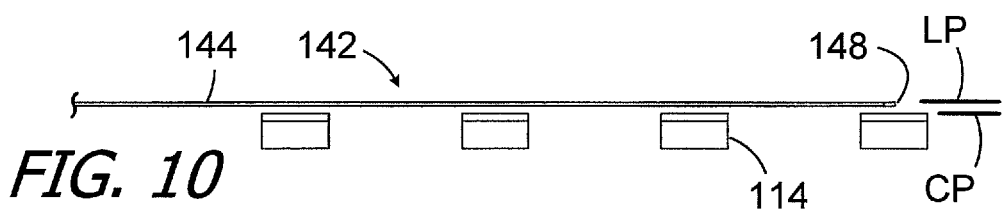
FIG. 10
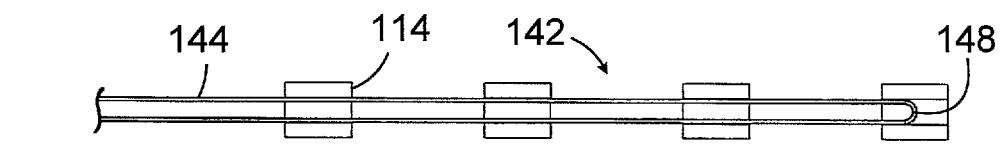
FIG. 11

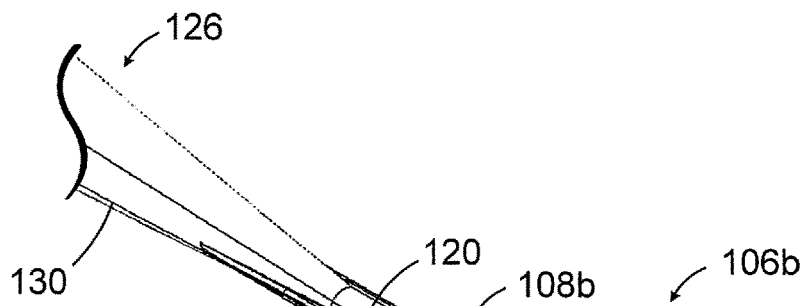
FIG. 21
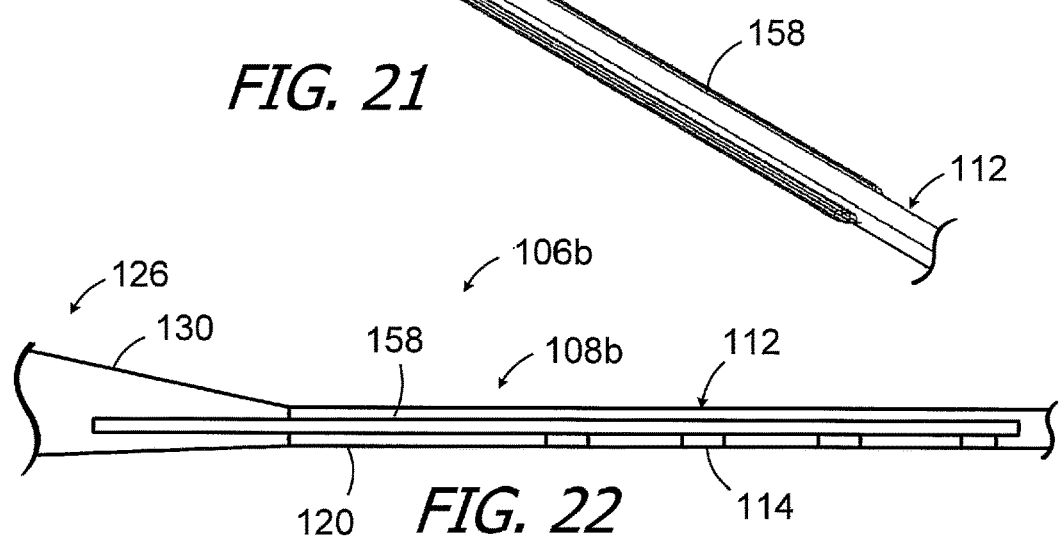
FIG. 22
FIG. 23
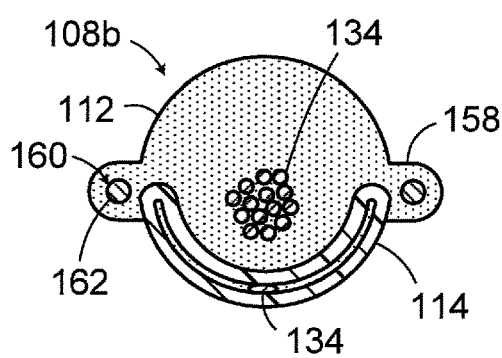
FIG. 24
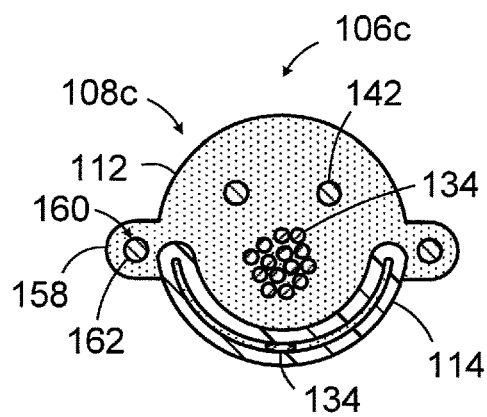
FIG. 25

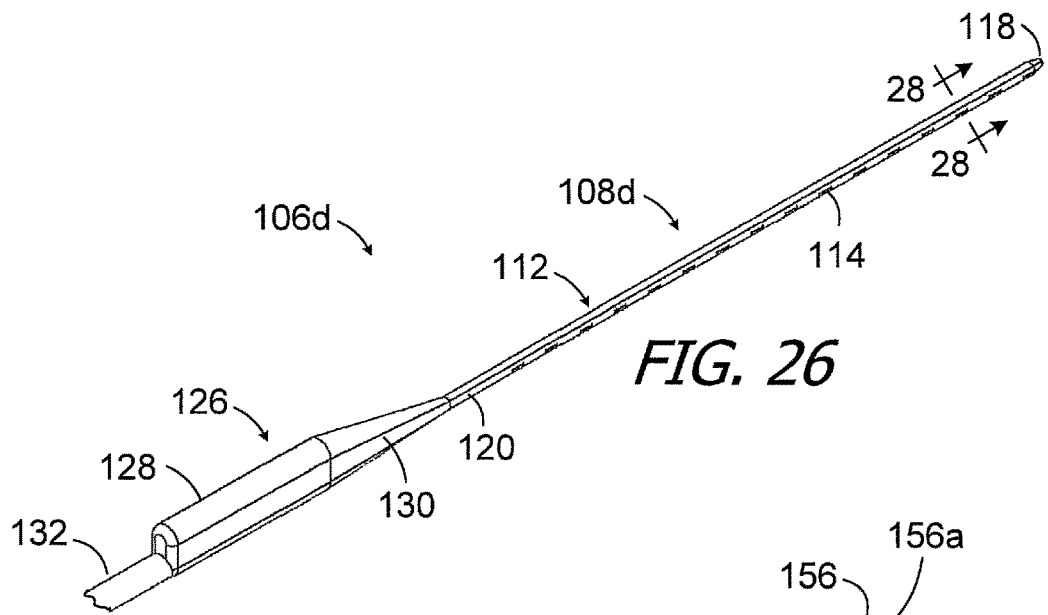
FIG. 26
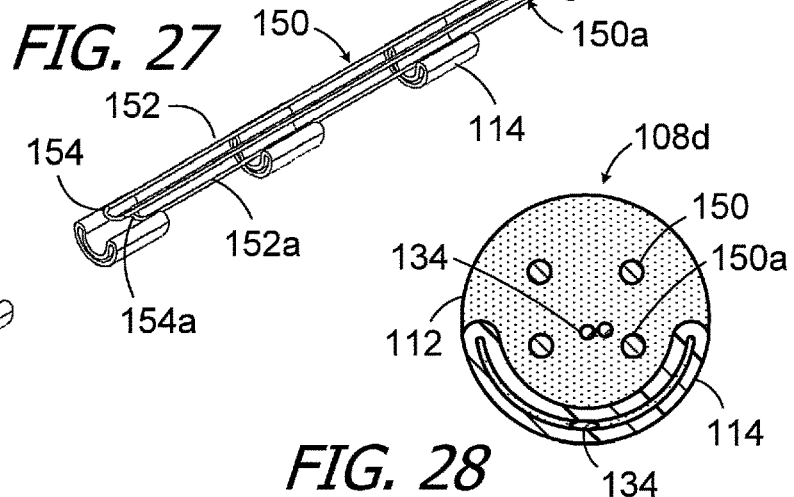
FIG. 27
FIG. 28
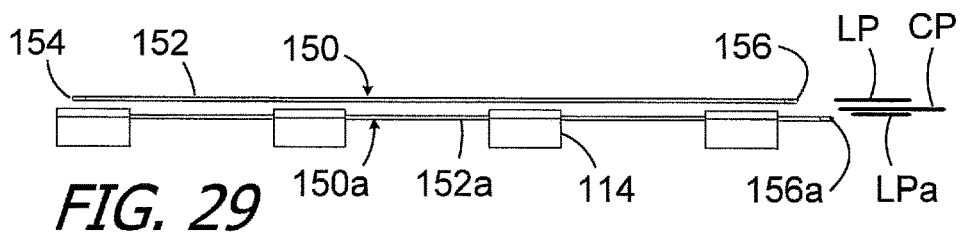
FIG. 29
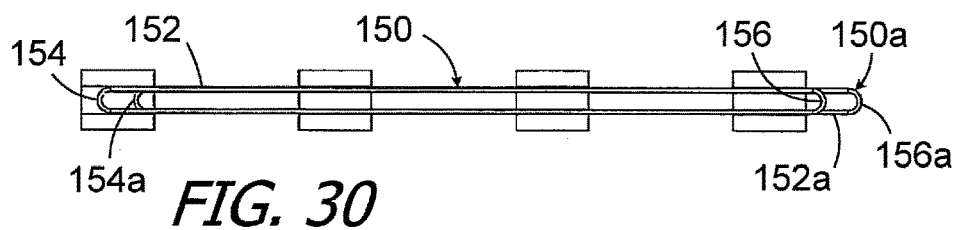
FIG. 30

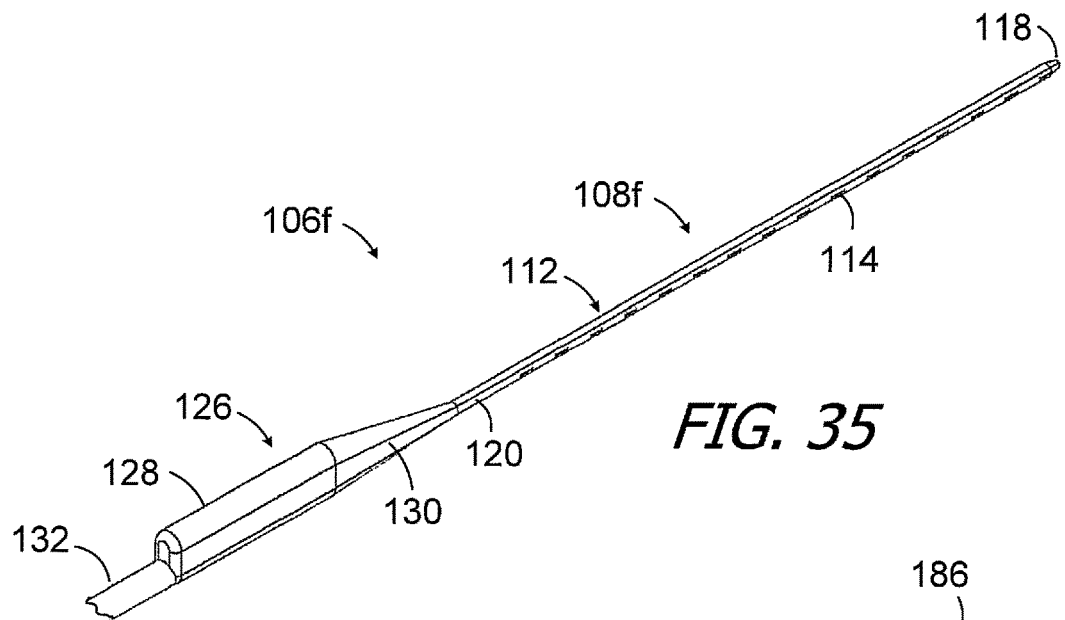
FIG. 35
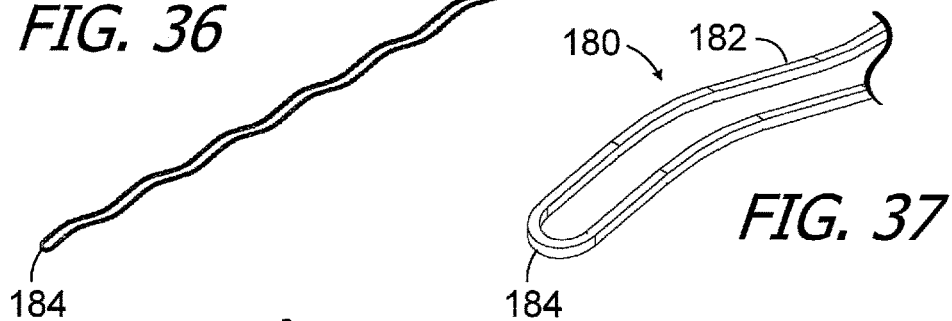
FIG. 36
FIG. 37
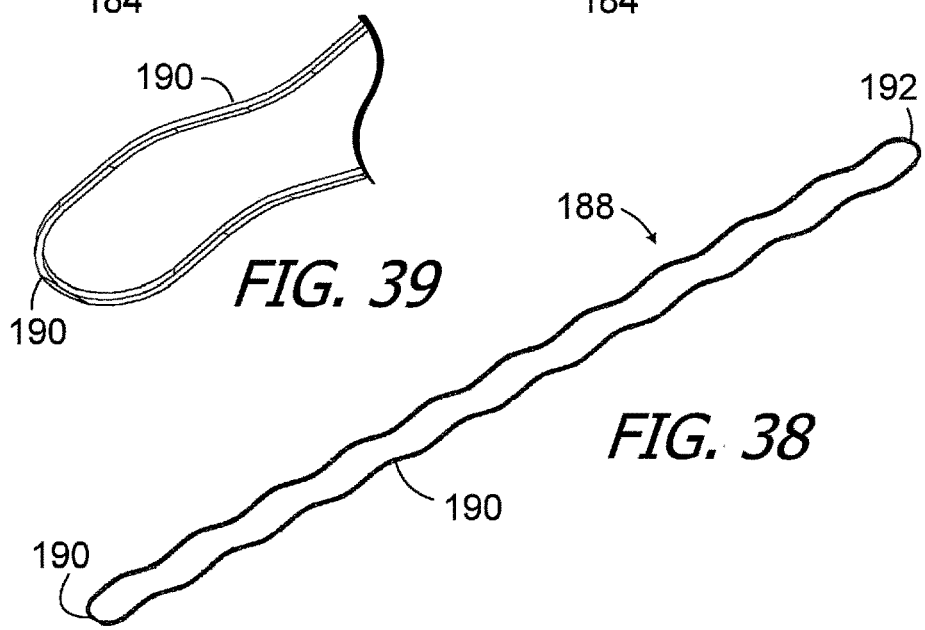
FIG. 39
FIG. 38

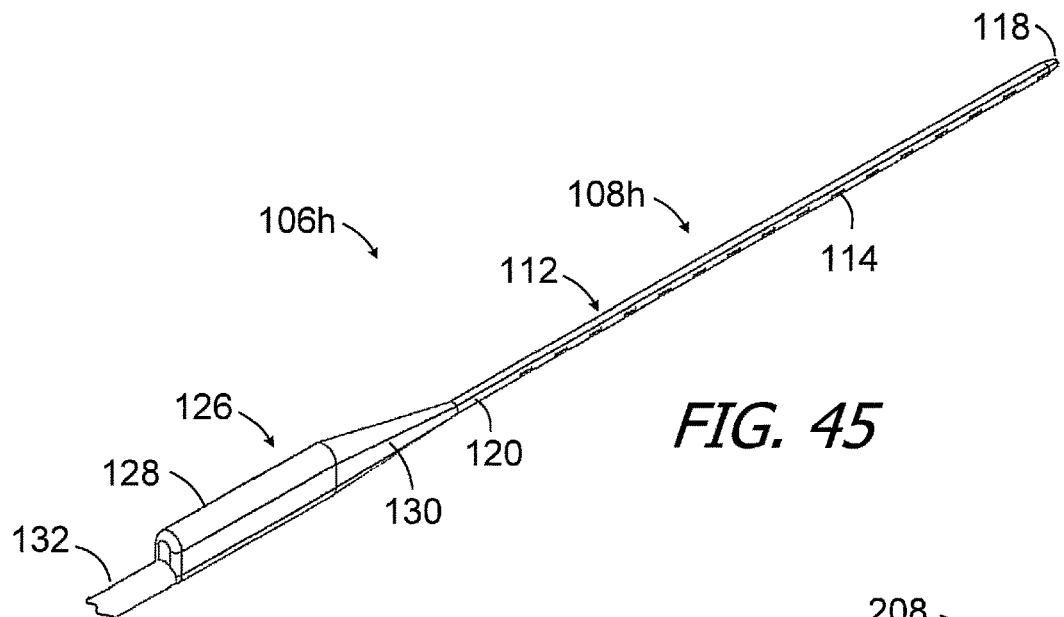
FIG. 45
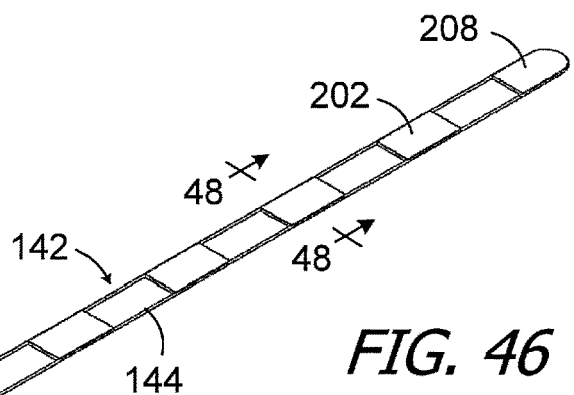
FIG. 46
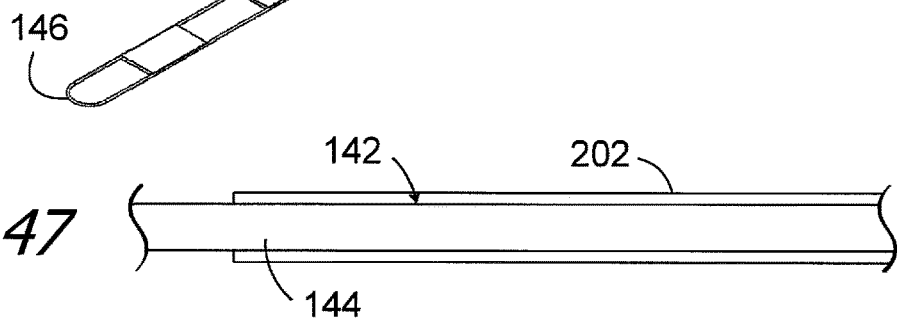
FIG. 47
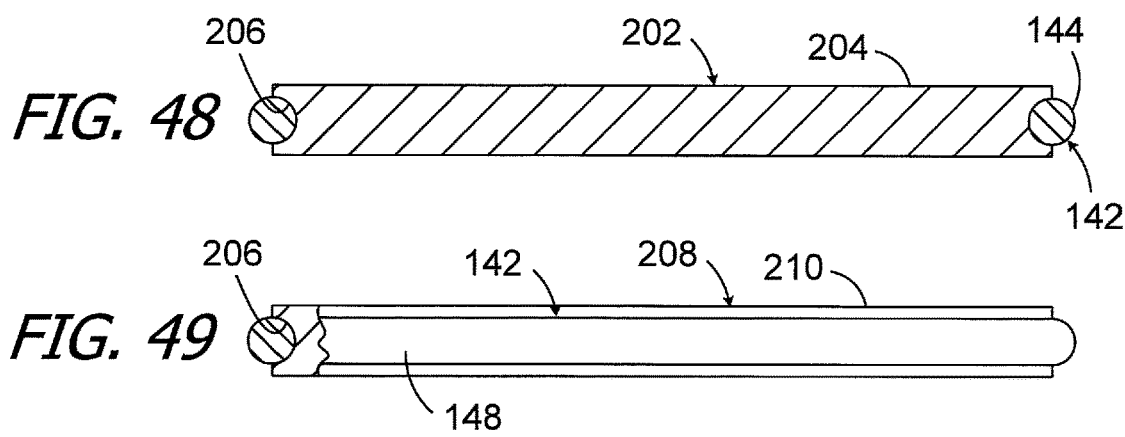
FIG. 48
FIG. 49

ELECTRODE ARRAYS AND COCHLEAR IMPLANTS INCLUDING THE SAME

CROSS-REFERENCE TO RELATED APPLICATIONS

This application a continuation of U.S. application Ser. No. 16/406,721, filed May 8, 2019, now U.S. Pat. No. 11,103,704, which is a continuation-in-part of, and claims priority to, International Application No. PCT/US2017/060030, filed Nov. 3, 2017, which claims priority to U.S. Prov. App. Ser. No. 62/419,349, filed Nov. 8, 2016, each of which are incorporated herein by reference in their entireties.

BACKGROUND

1. Field

The present disclosure relates generally to the implantable portion of implantable cochlear stimulation (or "ICS") systems and, in particular, to electrode arrays.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable lead with an electrode array that is inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant") having a lead with an electrode array, a sound processor unit (e.g., a body worn processor or behind-the-ear processor) that communicates with the cochlear implant, and a microphone that is part of, or is in communication with, the sound processor unit. The cochlear implant electrode array, which is formed by a molding process, includes a flexible body formed from a resilient material such as liquid silicone rubber ("LSR") and a plurality of electrically conductive contacts (e.g., sixteen platinum contacts) spaced along a surface of the flexible body. The contacts of the array are connected to platinum lead wires that extend through the flexible body. Once implanted, the contacts face the modiolus within the cochlea.

The present inventors have determined that conventional electrode arrays are susceptive to improvement. For example, conventional electrode arrays can buckle during the insertion process, which necessitates repositioning and can result in damage to any still functioning nerve endings in the cochlea that allow residual hearing to occur. In particular, when a thin electrode array (e.g., an electrode array with a diameter of about 0.33 mm in the apical-most region that gradually tapers up to about 0.6 mm to about 1.0 mm at the basal region) that is configured for placement against the lateral wall is inserted into an opening in the cochlea, such as an opening formed by the "round window" technique or a cochleostomy, the surface tension at the meniscus of the cochlea fluid may be sufficient to cause the distal tip the electrode array to deflect as the tip enters the opening. Additionally, the base portions of thin electrode arrays sometimes buckle mid-way through the insertion procedure. One conventional method of stiffening an electrode array so that it can resist buckling is to embed one or more rods or strips of relatively stiff material into the array. The present inventors have determined that, because such rods and strips tend to be sharp and point in the longitudinal direction, they can tear through the electrode array and/or damage the relatively fragile platinum wires. Moreover, such rods and strips can result in the mid-portion of the electrode array being too stiff to properly curl around the modiolus.

Exemplary methods of stiffening electrode arrays are disclosed in U.S. Pat. Nos. 8,249,724, 8,812,121, 8,880,193, 9,033,869, 9,037,267, and 9,492,654 and U.S. Pat. Pub. No. 2011/0137393.

SUMMARY

A cochlear implant in accordance with one of the present inventions may have a housing, an antenna, a stimulation processor operably connected to the antenna, and an electrode array, operably connected to the stimulation processor, including a flexible body defining a longitudinal axis, a proximal region and a distal region, a plurality of electrically conductive contacts on the flexible body, and at least one stiffener loop within the flexible body.

A cochlear implant in accordance with one of the present inventions may have a housing, an antenna, a stimulation processor operably connected to the antenna, and an electrode array, operably connected to the stimulation processor, including a flexible body defining a longitudinal axis, a proximal region and a distal region, a plurality of electrically conductive contacts on the flexible body, and at least one undulating stiffener within the flexible body and electrically isolated from the electrically conductive contacts.

A cochlear implant in accordance with one of the present inventions may have a housing, an antenna, a stimulation processor operably connected to the antenna, and an electrode array, operably connected to the stimulation processor, including a flexible body defining a longitudinal axis, a proximal region and a distal region, a plurality of electrically conductive contacts on the flexible body, and at least one multi-strand stiffener within the flexible body and electrically isolated from the electrically conductive contacts.

There are a number of advantages associated with cochlear implants having such electrode arrays. For example, the at least one stiffener prevents buckling of the associated portion of the electrode array without introducing a sharp edge into the array. The at least one stiffener loop defines a plane that controls bending of the array, as does the at least one undulating stiffener.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 6 is a section view taken along line 6-6 in FIG. 4.

FIG. 7 is a section view showing an exemplary contact configuration.

FIG. 8 is a top view of a portion of the cochlear lead illustrated in FIG. 1.

FIG. 9 is a perspective view of a portion of the cochlear lead illustrated in FIG. 1.

FIG. 10 is a side view of a portion of the cochlear lead illustrated in FIG. 1.

FIG. 11 is a top view of a portion of the cochlear lead illustrated in FIG. 1.

FIG. 21 is a perspective view of a portion of a cochlear lead in accordance with one embodiment of a present invention.

FIG. 22 is a side view of a portion of the cochlear lead illustrated in FIG. 21.

FIG. 23 is a bottom view of a portion of the cochlear lead illustrated in FIG. 21.

FIG. 24 is a section view taken along line 24-24 in FIG. 23.

FIG. 25 is a section view of a portion of a cochlear lead in accordance with one embodiment of a present invention.

FIG. 26 is a perspective view of a portion of a cochlear lead in accordance with one embodiment of a present invention.

FIG. 27 is a perspective view of a portion of the cochlear lead illustrated in FIG. 26.

FIG. 28 is a section view taken along line 28-28 in FIG. 26.

FIG. 29 is a side view of a portion of the cochlear lead illustrated in FIG. 27.

FIG. 30 is a top view of a portion of the cochlear lead illustrated in FIG. 27.

FIG. 35 is a perspective view of a portion of a cochlear lead in accordance with one embodiment of a present invention.

FIG. 36 a perspective view of the stiffener of the cochlear lead illustrated in FIG. 35.

FIG. 37 is a perspective view of a portion of the stiffener illustrated in FIG. 36.

FIG. 38 is a perspective view of a stiffener in accordance with one embodiment of a present invention.

FIG. 39 is a perspective view of a portion of the stiffener illustrated in FIG. 38.

FIG. 45 is a perspective view of a portion of a cochlear lead in accordance with one embodiment of a present invention.

FIG. 46 is a perspective view of a portion of the cochlear lead illustrated in FIG. 45.

FIG. 47 is a side view of the portion of the cochlear lead illustrated in FIG. 46.

FIG. 48 is a section view taken along line 48-48 in FIG. 46.

FIG. 49 is an end view of the portion of the cochlear lead illustrated in FIG. 46.

DETAILED DESCRIPTION OF THE EXEMPLARY EMBODIMENTS

Figure 1:
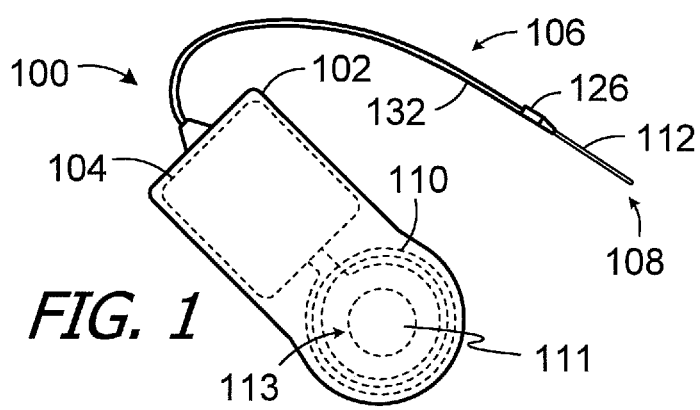
FIG. 1 is a plan view of a cochlear implant in accordance with one embodiment of a present invention.

The following is a detailed description of the best presently known modes of carrying out the inventions. This description is not to be taken in a limiting sense, but is made merely for the purpose of illustrating the general principles of the inventions.

One example of a cochlear implant (or "implantable cochlear stimulator") in accordance with at least some of the present inventions is illustrated in FIGS. 1-5. The cochlear implant 100 includes a flexible housing 102 formed from a silicone elastomer or other suitable material, a processor assembly 104, a cochlear lead 106 with an electrode array 108, and an antenna 110 that may be used to receive data and power by way of an external antenna that is associated with, for example, a sound processor unit. A positioning magnet 111 (FIG. 1) is located within a magnet pocket 113. The magnet 111 is used to maintain the position of a headpiece transmitter over the antenna 110. The cochlear implant may, in some instances, be configured is manner that facilitates magnet removal and replacement. Here, the housing 102 may be provided with a magnet aperture (not shown) that extends from the magnet pocket 113 to the exterior of the housing.

The electrode array 108 includes a flexible body 112 and a plurality of electrically conductive contacts 114 (e.g., the sixteen contacts 114 illustrated in FIG. 4) spaced along the bottom surface 116 of the flexible body. Suitable materials for the flexible body 112 include, but are not limited to, LSR, high temperature vulcanization ("HTV") silicone rubbers, room temperature vulcanization ("RTV") silicone rubbers, and thermoplastic elastomers ("TPEs"), while suitable materials for the contacts 114 include, but are not limited to, platinum, platinum-iridium, gold and palladium. The contacts 114 may be referred to in numbered order, $1^{st}$ through $16^{th}$, with the contact closest to the tip 118 being the $1^{st}$ contact and the contact closest to the base 120 being the $16^{th}$ contact. The exemplary flexible body 112 also includes a longitudinally extending top surface 122 that does not include conductive contacts. Once implanted, the conductive contacts 114 on the curved surface 116 face the modiolus within the cochlea.

Figure 2:
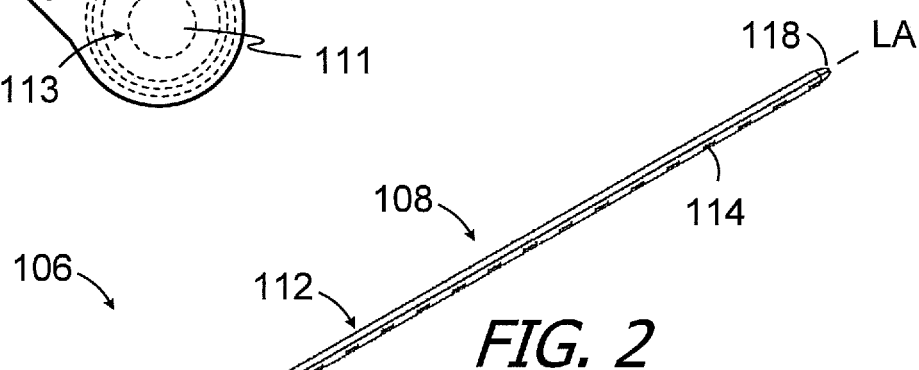
FIG. 2 is a perspective view of a portion of the cochlear lead illustrated in FIG. 1.
Figure 5:
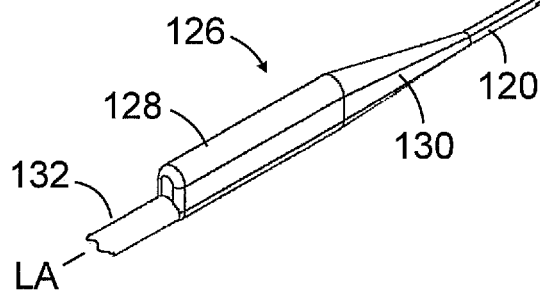
FIG. 5 is a section view taken along line 5-5 in FIG. 4.
Figure 3:
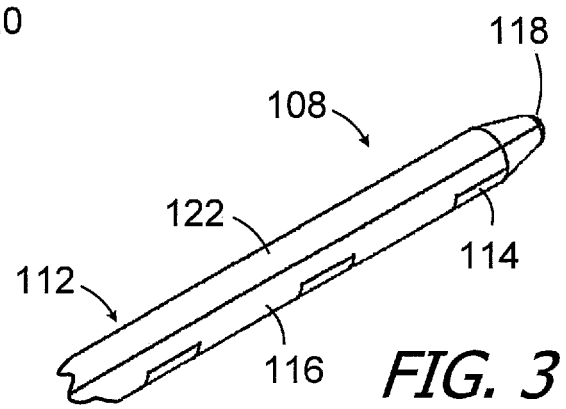
FIG. 3 is a perspective view of a portion of the cochlear lead illustrated in FIG. 1.
Figure 4:
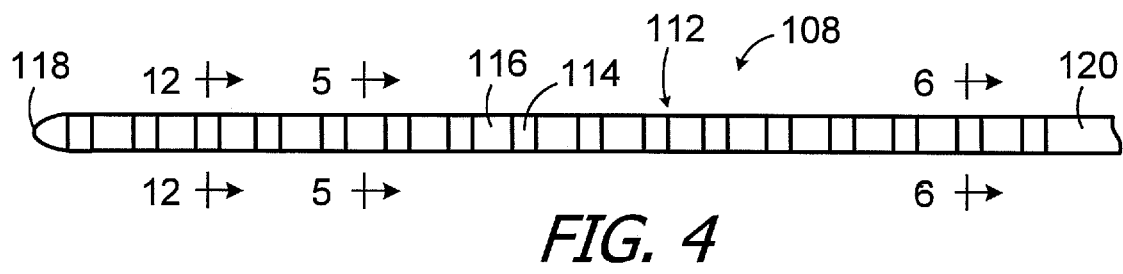
FIG. 4 is a bottom view of a portion of the cochlear lead illustrated in FIG. 1.
Figure 12:
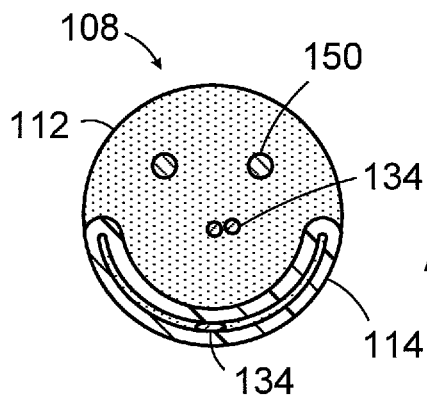
FIG. 12 is a section view taken along line 12-12 in FIG. 4.
Figure 13:
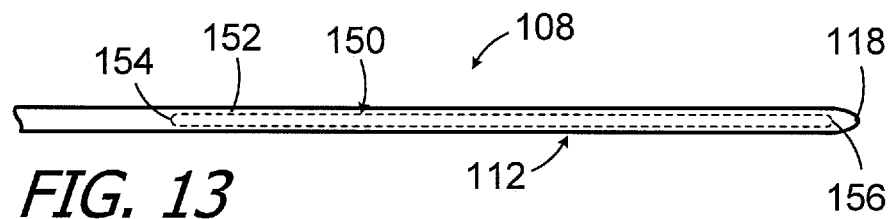
FIG. 13 is a top view of a portion of the cochlear lead illustrated in FIG. 1.
Figure 14:
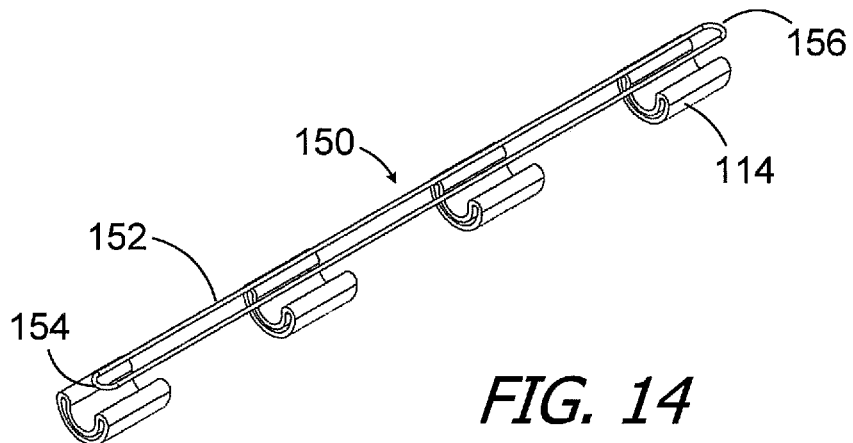
FIG. 14 is a perspective view of a portion of the cochlear lead illustrated in FIG. 1.
Figure 14:
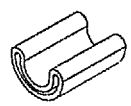
Figure 15:
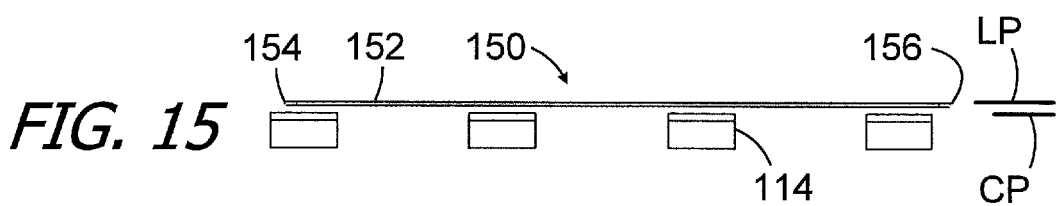
FIG. 15 is a side view of a portion of the cochlear lead illustrated in FIG. 1.
Figure 16:
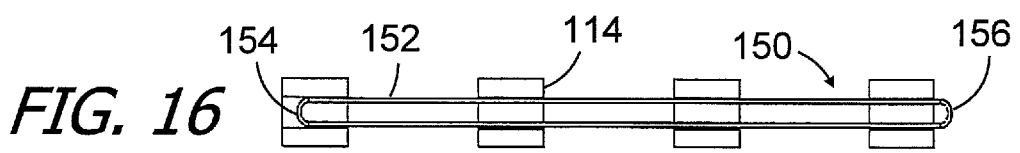
FIG. 16 is a top view of a portion of the cochlear lead illustrated in FIG. 1.

The exemplary flexible body 112 has a circular shape in a cross-section perpendicular to the longitudinal axis LA of the electrode array 108 (FIGS. 2 and 5). In other implementations, a truncated circular shape, with a flat top surface, may be employed.

Turning to FIG. 2, in addition to the electrode array 108, the exemplary cochlear lead 106 includes a handle 126, with a rectangular portion 128 and a tapered portion 130, which may be gripped by the surgeon during the implantation surgery. The handle 126 also provides tension relief for the lead wires 134, which do not run straight through the handle. A tubular member 132, which may consist of tubes of different sizes, extends from the handle 126 to the housing 102. The contacts 114 are connected to lead wires 134 (FIG. 5) that extend through the flexible body 112 and tubular member 132 to a connector (not shown) in the housing 102. The lead wires 134 may be formed from, for example, platinum-iridium or other suitable materials.

Turning to FIG. 6, the contacts 114 in the illustrated implementation are formed by placing a tubular workpiece into a mold, positioning the lead wire 134 that will be connected to that contact within the workpiece, and then applying heat and pressure to the workpiece to form a semi-circular contact that is connected to a lead wire. A small gap may remain between portions of the contacts 114. The gaps augment the mechanical interconnection between the flexible body 112 and the contacts 114. Alternatively, as illustrated in FIG. 7, the compression and distortion of the malleable workpiece may cause the opposing portions workpiece to come into contact with one another along a seam 140 in the otherwise identical electrode array 108'. In either case, the contact formation process is repeated until all of the contacts are formed in the mold. The mold is then covered and resilient material is injected into the mold to form the flexible body 112.

The exemplary electrode array 108 and other electrode arrays 108a-108m described below are also provided with various structures that stiffen the proximal region of the electrode array and/or the distal region of the electrode array to prevent buckling. The structures also control bending and prevent unwanted rotation of those regions of the electrode array.

Referring first to FIGS. 6-11, the proximal region of the exemplary electrode array 108 includes a stiffener loop 142 that is embedded within the flexible body 112. In the illustrated implementation, the stiffener loop 142 is located within the handle tapered portion 130 and the portion of the flexible body 112 adjacent to be base 120. The exemplary stiffener loop 142 is a closed loop that includes a pair of longitudinally extending side members 144 as well as proximal and distal curved end members 146 and 148 that are connected to the side members. The stiffener loop 142 is offset from, and is coextensive with, the four contacts 114 that are adjacent to the base 120, i.e., contacts thirteen to sixteen in the illustrated sixteen contact embodiment. The stiffener loop 142 also defines a loop plane LP that may be parallel to the contact plane CP defined by the top ends (in the illustrated orientation) of the contacts 114. In addition to preventing buckling at or near the base 120, the stiffener loop 142 controls the direction that the flexible body 112 bends, thereby preventing unwanted rotation of the flexible body during insertion, by virtue of the orientation of the loop plane LP. Alternate loop plane orientations may be employed as necessary.

It should also be noted that the stiffener loop 142 is electrically isolated from the electrically conductive contacts 114, as are the other stiffener loops and other types of stiffeners described below. Moreover, as used herein, a "stiffener" is not a lead wire (such as a lead wire 134), or a plurality of lead wires, that electrically connects one or more electrically conductive contacts to a source of electrical stimulation current.

The longitudinally extending side members 144 (and other side members discussed below) are parallel to one another and to the longitudinal axis LA. In other implementations, the distance between the longitudinally extending side members may increase, or decrease, from the proximal curved end member to the distal curved end member.

Turning to FIGS. 12-16, the distal region of the exemplary electrode array 108 includes a stiffener loop 150 that is embedded within the flexible body 112. The configuration of the stiffener loop 150 may be the same as the stiffener loop 142 (as shown) or different than the stiffener loop 142. In the illustrated implementation, the stiffener loop 150 is located adjacent to the tip 118. The exemplary stiffener loop 150 includes a pair of longitudinally extending side members 152 as well as proximal and distal curved end members 154 and 156 that are connected to the side members. The stiffener loop 150 offset from, and is coextensive with, the four contacts 114 that are adjacent to the tip 118, i.e., contacts one to four in the illustrated sixteen contact embodiment. The stiffener loop 150 also defines a loop plane LP that may be parallel to the contact plane CP defined by the top ends of the contacts 114. In addition to preventing buckling at or near the tip 118, the stiffener loop 150 controls the direction that the flexible body 112 bends, thereby preventing unwanted rotation of the flexible body, by virtue of the orientation of the loop plane LP. Alternate loop plane orientations may be employed as necessary.

It should also be noted here that the curved stiffener loop ends 148, 154 and 154 lack sharp edges. As such, they are less likely than a conventional stiffener to tear through flexible body 112.

Figure 17:
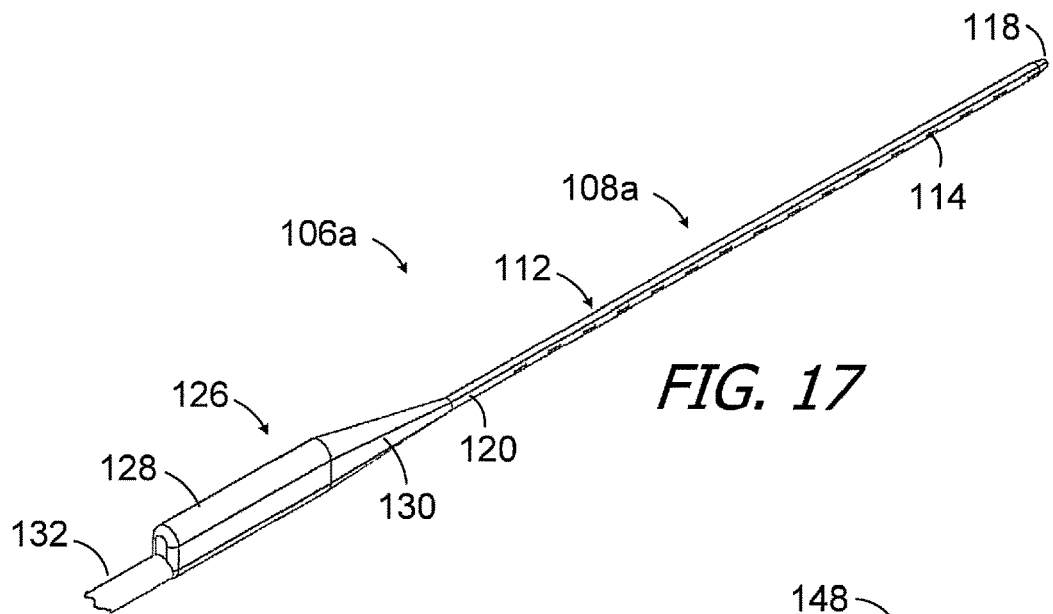
FIG. 17 is a perspective view of a portion of a cochlear lead in accordance with one embodiment of a present invention.
Figure 18:
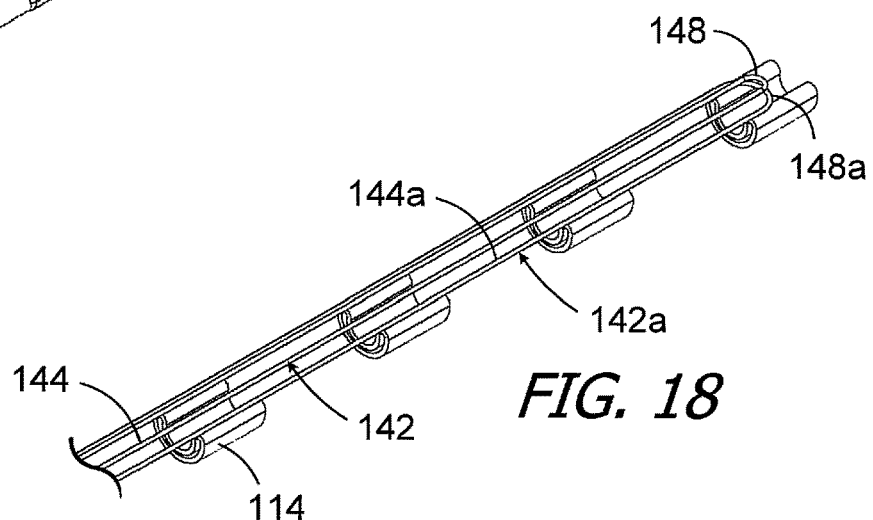
FIG. 18 is a perspective view of a portion of the cochlear lead illustrated in FIG. 17.
Figure 19:
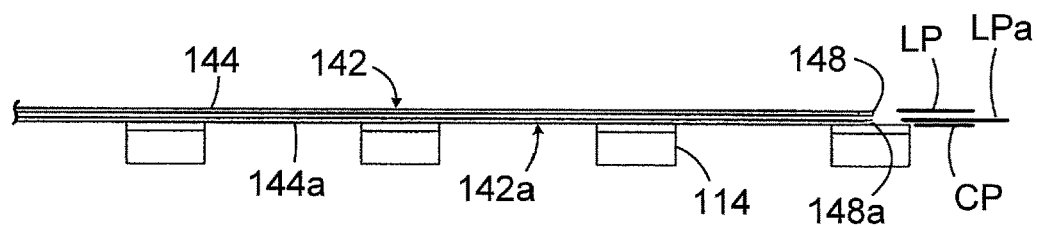
FIG. 19 is a side view of the portion of the cochlear lead illustrated in FIG. 18.
Figure 20:
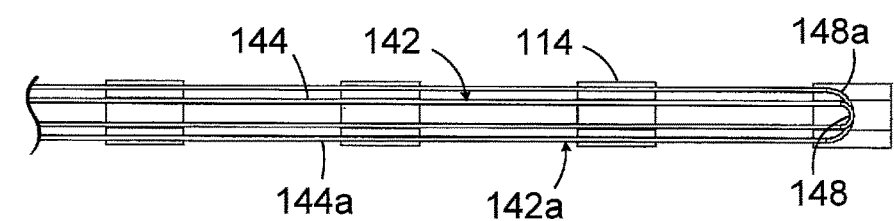
FIG. 20 is a top view of the portion of the cochlear lead illustrated in FIG. 18.
Figure 31:
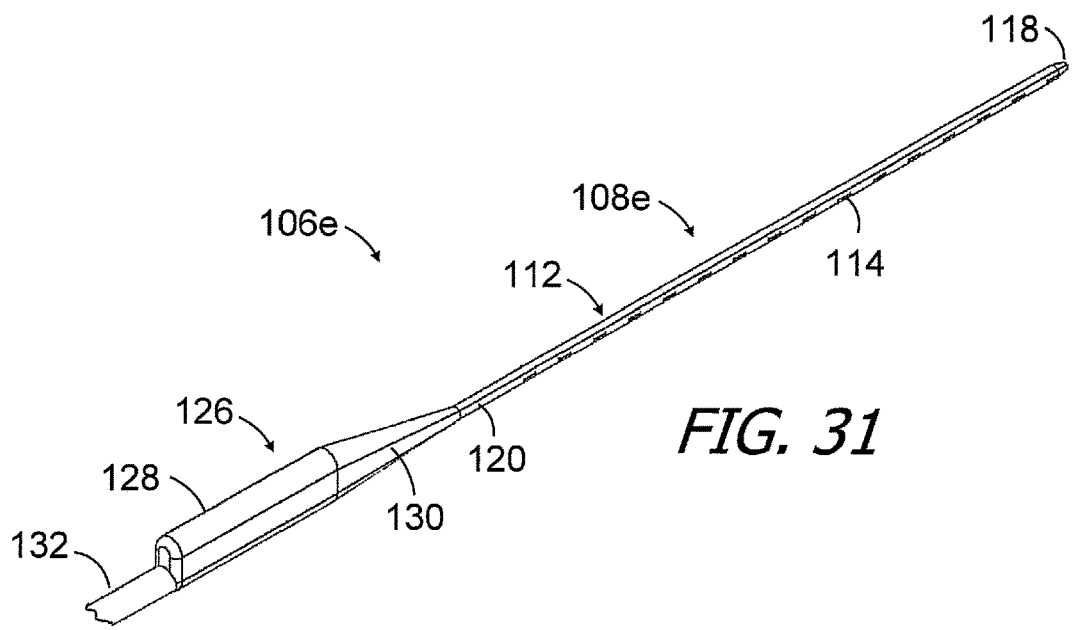
FIG. 31 is a perspective view of a portion of a cochlear lead in accordance with one embodiment of a present invention.
Figure 32:
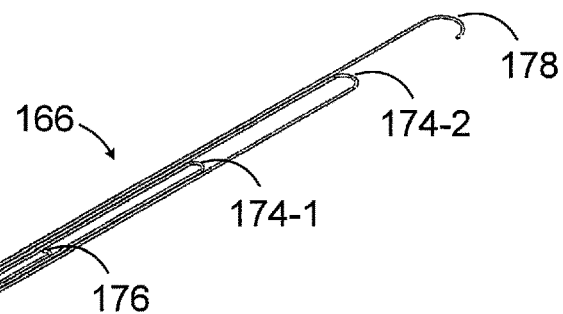
FIG. 32 is a perspective view of the stiffener of the cochlear lead illustrated in FIG. 31.
Figure 33:
FIG. 33 is a top view of a portion of the stiffener illustrated in FIG. 32.
Figure 33:
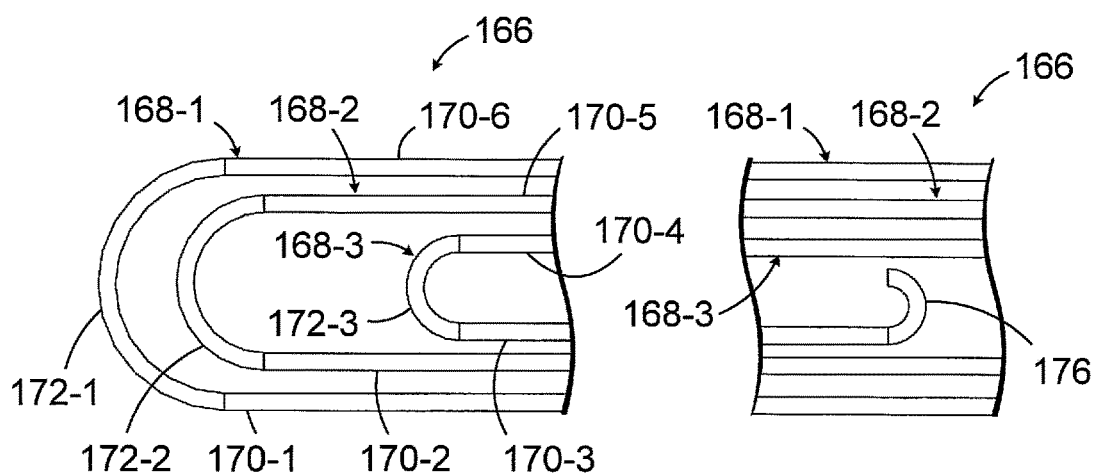
Figure 34:
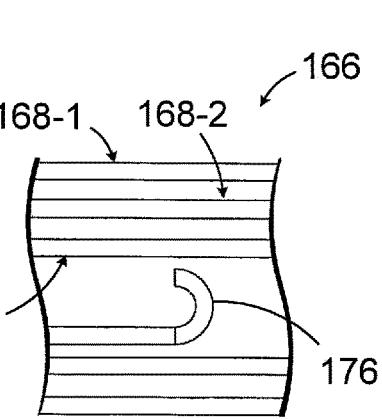
FIG. 34 is a top view of a portion of the stiffener illustrated in FIG. 32.
Figure 40:
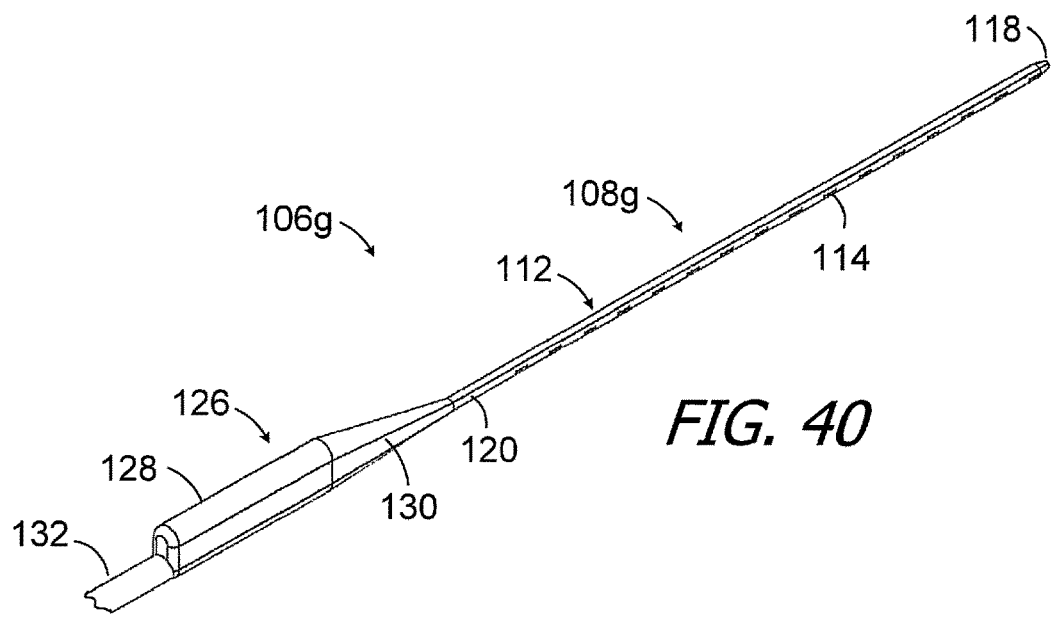
FIG. 40 is a perspective view of a portion of a cochlear lead in accordance with one embodiment of a present invention.
Figure 41:
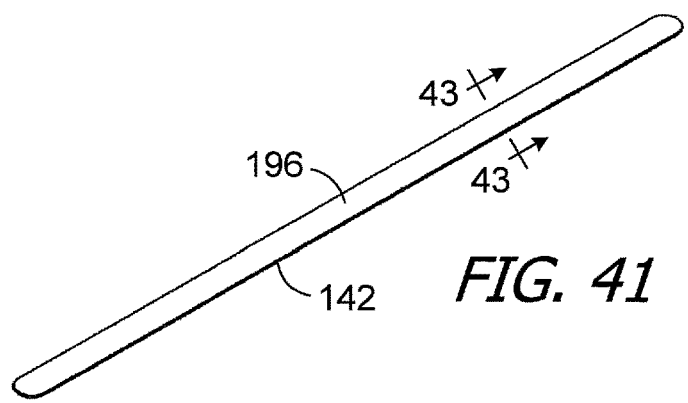
FIG. 41 is a perspective view of a portion of the cochlear lead illustrated in FIG. 40.
Figure 42:
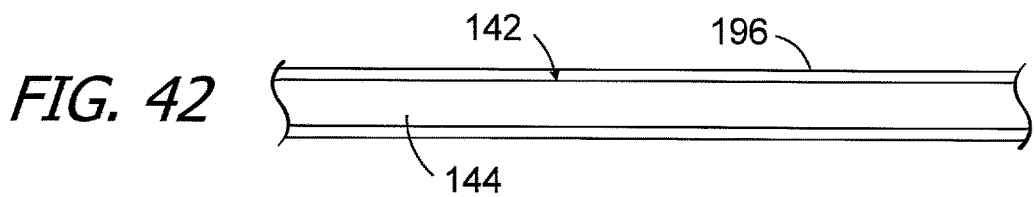
FIG. 42 is a side view of the portion of the cochlear lead illustrated in FIG. 41.
Figure 43:
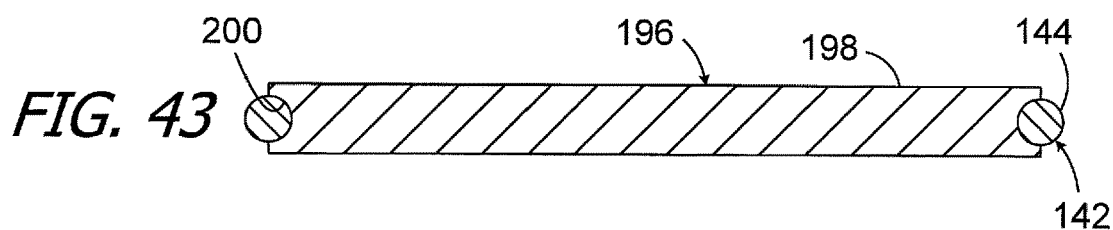
FIG. 43 is a section view taken along line 43-43 in FIG. 41.
Figure 44:
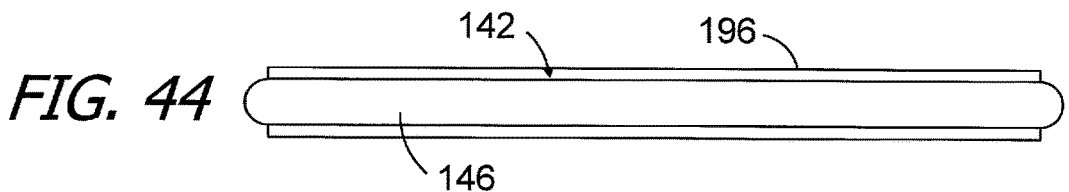
FIG. 44 is an end view of the portion of the cochlear lead illustrated in FIG. 41.
Figure 50:
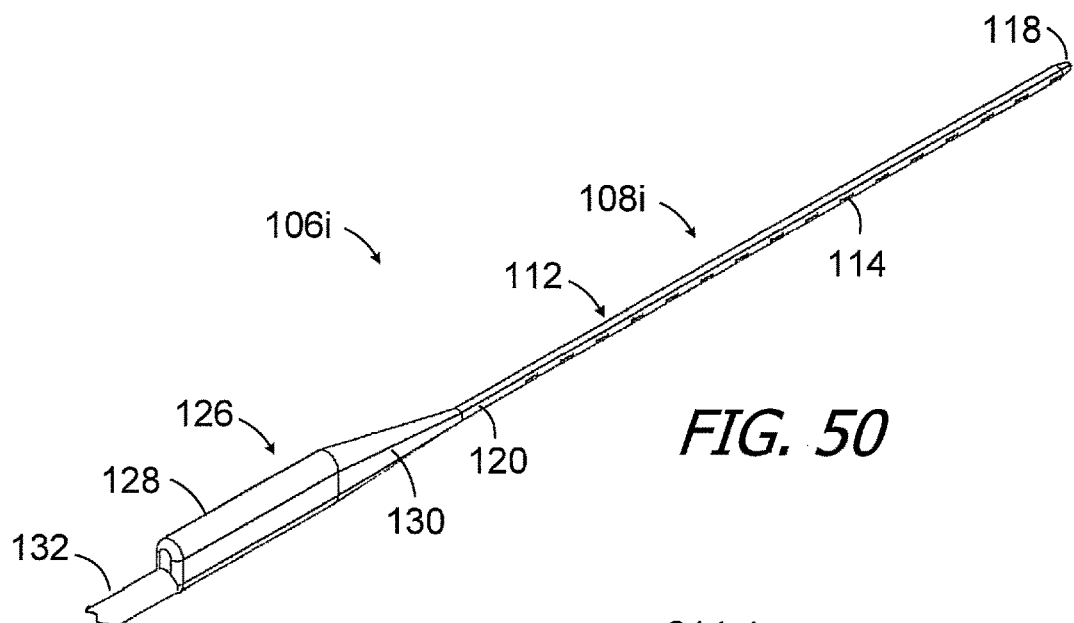
FIG. 50 is a perspective view of a portion of a cochlear lead in accordance with one embodiment of a present invention.
Figure 51:
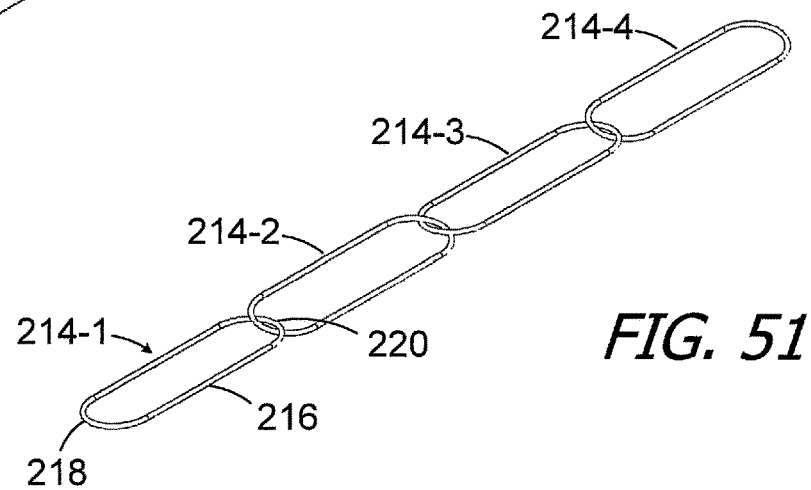
FIG. 51 is a perspective view of the stiffener of the cochlear lead illustrated in FIG. 50.
Figure 52:
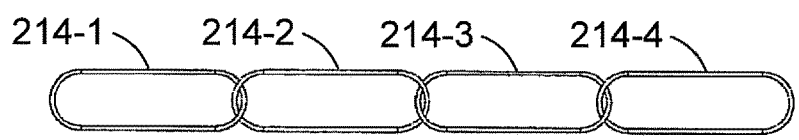
FIG. 52 is a top view of the stiffener illustrated in FIG. 51.
Figure 53:
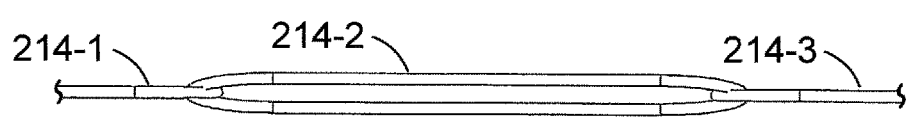
FIG. 53 is a side view of the stiffener illustrated in FIG. 51.
Figure 54:
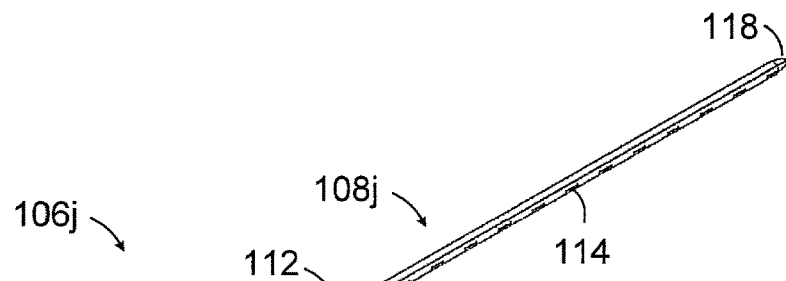
FIG. 54 is a perspective view of a portion of a cochlear lead in accordance with one embodiment of a present invention.

With respect to materials, suitable materials for the stiffener loops 142 and 150 (as well as the stiffeners described below with reference to FIGS. 17-69) include, but are not limited to, drawn filled tubing such as DFT® wire. Suitable drawn filled tubing examples include a core metal, such as platinum, palladium, silver or gold, with an outer material, such as Nitinol or the nickel-cobalt alloy sold under the tradename MP35N®. Other suitable material examples are titanium, stainless steel, carbon nanotubes and silica glass.

The exemplary cochlear lead 106 may be modified in variety of ways. To that end, and referring to FIGS. 17-20, the exemplary cochlear lead 106a is substantially similar to cochlear lead 106 and similar elements are represented by similar reference numerals. Here, however, the proximal region of the exemplary electrode array 108a includes a pair of stiffener loops 142 and 142a that are embedded in the flexible body 112. In the illustrated implementation, the stiffener loops 142 and 142a are located within the handle tapered portion 130 and the portion of the flexible body 112 adjacent to be base 120. The exemplary stiffener loop 142a includes a pair of longitudinally extending side members 144a, a proximal curved end member (not shown) and a distal curved end member 148a. The stiffener loop 142a is either slightly offset from (as shown) or rests on, and is coextensive with, the four contacts 114 that are adjacent to the base 120, i.e., the contacts thirteen to sixteen in the illustrated sixteen contact embodiment, and is located between the stiffener loop 142 and the contacts. The stiffener loop 142a is also slightly wider than the stiffener loop 142 in that the distance between the side members 144a is greater that the distance between the side members 144.

In other implementations, the wider stiffener loop 142a may be employed in place of (i.e., without) the stiffener loop 142. The stiffener loop 142a may be formed from the same material as the stiffener loop 142, when used together, and/or from the same material as the stiffener loop 150, and/or from a different material the stiffener loop 142 or the stiffener loop 150. The wider stiffener loop 142a, with or without the stiffener loop 142, may also be incorporated into the cochlear leads 106b-106d described below with reference to FIGS. 21-30.

Another exemplary cochlear lead, which is generally represented by reference numeral 106b, is illustrated in FIGS. 21-24. The exemplary cochlear lead 106b is substantially similar to cochlear lead 106 and similar elements are represented by similar reference numerals. Here, however, the proximal region of the exemplary electrode array 108b includes a pair of side wings 158 that extend laterally from the flexible body 112 and the handle tapered portion 130. The side wings 158 extend to the fourth contact 114 from the base 120, i.e., contact thirteen in the illustrated sixteen contact embodiment, although the length of side wings may be increased or decreased as necessary. The side wings 158 prevent buckling at or near the base 120 and also control the direction that the flexible body 112 bends, thereby preventing unwanted rotation of the flexible body.

The stiffness of the side wings 158 may be augmented through the use of a stiffener loop 160 that is embedded in the exemplary electrode array 108b. The stiffener loop 160 is located within the side wings 158 and includes a pair of longitudinally extending side members 162, a proximal curved end member (not shown) and a distal curved end member 164. In other exemplary embodiments, an additional stiffener loop may be provided. To that end, and referring to FIG. 25, the exemplary cochlear lead 106c (which is otherwise identical to cochlear lead 106b) includes an electrode array 108c with a stiffener loop 142 in addition to the side wings 158 and stiffener loop 160. The stiffener loop 160 may be formed from the same material as the stiffener loop 142 or from a different material. It should also be noted here that, in other implementations, the cochlear leads described above with reference to FIGS. 21-25 may include the distal regions described below with reference to FIGS. 26-30.

Another exemplary cochlear lead, which is generally represented by reference numeral 106d, is illustrated in FIGS. 26-30. The exemplary cochlear lead 106d is substantially similar to cochlear lead 106 and similar elements are represented by similar reference numerals. Here, however, the distal region of the exemplary electrode array 108d has a pair of stiffener loops 150 and 150a that are embedded in the flexible body 112. The stiffener loop 150a, which includes a pair of longitudinally extending side members 152a as well as proximal and distal curved end members 154a and 156a, may have the same configuration as the stiffener loop 150 (as shown) or different configuration. The stiffener loop 150a is located adjacent to the tip 118 and is offset slightly in the distal direction from the stiffener loop 150. The stiffener loop 150a, which defines a loop plane LPa, is also located below the top ends (in the illustrated orientation) of the contacts 114. The loop plane LPa may be parallel to the contact plane CP defined by the ends of the contacts 114 and the loop plane LP. In addition to preventing buckling at or near the tip 118, the stiffener loops 150 and 150a control the direction that the flexible body 112 bends, thereby preventing unwanted rotation of the flexible body, by virtue of the orientation of the loop planes LP and LPa. Alternate loop plane orientations may be employed as necessary, and the stiffener loop 150 may also be omitted in some implementations.

Another exemplary cochlear lead, which is generally represented by reference numeral 106e, is illustrated in FIGS. 31-34. The exemplary cochlear lead 106e is substantially similar to cochlear lead 106 and similar elements are represented by similar reference numerals. Here, however, the proximal region of the exemplary electrode array 108e includes a stiffener loop 166 with a plurality of turns that is embedded in the flexible body 112. The stiffener loop 166 is an open loop (i.e., a loop with free ends) that defines a plane that may be parallel to the contact plane, or may be in other orientations, as is described above. In the illustrated implementation, the stiffener loop is located within the handle tapered portion 130 and the portion of the flexible body 112 adjacent to be base 120. The exemplary stiffener loop 166 includes three turns 168-1, 168-2 and 168-3. The turns 168-1, 168-2 and 168-3 are defined by a pair of longitudinally extending side members 170-1 to 170-6, proximal curved end members 172-1, 172-2 and 172-3 and distal curved end members 174-1 and 174-2. The exemplary stiffener loop 166 also has curved free ends 176 and 178. The stiffener loop 166 may either be slightly offset from, or rest on, the associated contacts 114.

The stiffness of the stiffener loop 166 is not constant along the length of the stiffener loop. In the illustrated implementation, the stiffness of the stiffener loop 166 decreases from the proximal (or "basal") region to the distal (or "apical") region. For example, the stiffness at a location where all six of the longitudinally extending side members 170-1 to 170-6 are present (i.e., at a location between the proximal curved end member 172-3 and the curved free end 176) is greater than the stiffness at a location where fewer longitudinally extending side members are present (e.g., at a location between the distal curved end members 174-1 and 174-2).

The exemplary stiffener loop 166 may in some instances be coextensive with the four contacts 114 that are adjacent to the base 120, i.e., the contacts thirteen to sixteen in the illustrated sixteen contact embodiment, in a manner similar to that illustrated in FIGS. 8 and 9. Alternatively, or in addition, a stiffener loop 166 may be located adjacent to the tip 118. Here, the stiffener loop 166 may in some instances be offset from, and coextensive with, the four contacts 114 that are adjacent to the tip 118, i.e., contacts one to four in the illustrated sixteen contact embodiment, in a manner similar to that illustrated in FIGS. 13 and 14. In still other implementations, a pair of stiffener loops 166, with either the same or different dimensions as one another, may be employed adjacent to the base 120 and/or adjacent to the tip 118 in, for example, the manners described above with reference to FIGS. 17-20 and 26-30.

Another exemplary cochlear lead, which is generally represented by reference numeral 106f, is illustrated in FIGS. 35-37. The exemplary cochlear lead 106f is substantially similar to cochlear lead 106 and similar elements are represented by similar reference numerals. Here, however, the proximal region of the exemplary electrode array 108f includes an undulating (or wave-shaped) stiffener loop 180 that is embedded in the flexible body 112. The stiffener loop plane (i.e., the plane that extends longitudinally through the midpoints of the waves) may be parallel to the contact plane, or may be in other orientations, as is described above. In the illustrated implementation, the stiffener loop is located within the handle tapered portion 130 and the portion of the flexible body 112 adjacent to be base 120. The exemplary stiffener loop 180 includes a pair of longitudinally extending undulating side members 182, a proximal curved end member 184 and a distal curved end member 186. The side members 182 undulate toward and away from the contacts 114. The undulating stiffener loop 180 may either be slightly offset from, or rest on, the associated contacts 114.

The exemplary undulating stiffener loop 180 may in some instances be coextensive with the four contacts 114 that are adjacent to the base 120, i.e., the contacts thirteen to sixteen in the illustrated sixteen contact embodiment, in a manner similar to that illustrated in FIGS. 8 and 9. Alternatively, or in addition, an undulating stiffener loop 180 may be located adjacent to the tip 118. Here, the stiffener loop 180 may in some instances be offset from, and coextensive with, the four contacts 114 that are adjacent to the tip 118, i.e., contacts one to four in the illustrated sixteen contact embodiment, in a manner similar to that illustrated in FIGS. 13 and 14. In still other implementations, a pair of stiffener loops 180, with either the same or different dimensions as one another, may be employed adjacent to the base 120 and/or adjacent to the tip 118 in, for example, the manners described above with reference to FIGS. 17-20 and 26-30.

The exemplary stiffener loop 180 is also relatively narrow and is sized relative to the flexible body 112 and contacts 114 in a manner similar to that illustrated in FIGS. 6, 8 and 11 in the context of stiffener loop 142. The exemplary undulating stiffener loop 188 illustrated in FIGS. 38 and 39, which includes a pair of longitudinally extending undulating side members 190, a proximal curved end member 192 and a distal curved end member 194, is relatively wide. The stiffener loop 188 may be employed in, for example, an electrode array with a pair of side wings similar to the electrode array described above with reference to FIGS. 21-25.

Another exemplary cochlear lead, which is generally represented by reference numeral 106g, is illustrated in FIGS. 40-44. The exemplary cochlear lead 106g is substantially similar to cochlear lead 106 and similar elements are represented by similar reference numerals. Here, however, a support 196 is attached to the above-described stiffener loop 142 that is located the proximal region of the exemplary electrode array 108g. The support 196 augments the bending control aspect of the associated portion of the electrode array 108g, as compared to an otherwise identical electrode array without the support. The stiffener loop 142 and support 196 define a plane that may be parallel to the contact plane, or may be in other orientations, as is described above. In the illustrated implementation, the stiffener loop 142 and support 196 are located within the handle tapered portion 130 and the portion of the flexible body 112 adjacent to be base 120. The exemplary support 196, which includes a main body 198 and a groove 200 in which the stiffener loop 142 is located, may be a one-piece structure that is coextensive with the entire stiffener loop 142. The groove 200 extends completely around the main body 198 and, accordingly, the stiffener loop side members 144 as well as proximal and distal curved end members 146 and 148 are located within the groove. The support 196 may be molded onto the stiffener loop 142. Suitable materials for the support 196 include, but are not limited to, polytetrafluoroethylene (PTFE) and polyetheretherketone (PEEK).

The stiffener loop 142 and support 196 may either be slightly offset from, or rest on, the associated contacts 114. The stiffener loop 142 and support 196 may in some instances be coextensive with the four contacts 114 that are adjacent to the base 120, i.e., the contacts thirteen to sixteen in the illustrated sixteen contact embodiment, in a manner similar to that illustrated in FIGS. 8 and 9. Alternatively, or in addition, a stiffener loop 142 and a support 196 may be located adjacent to the tip 118. Here, the stiffener loop 142 and support 196 may in some instances be offset from, and coextensive with, the four contacts 114 that are adjacent to the tip 118, i.e., contacts one to four in the illustrated sixteen contact embodiment, in a manner similar to that illustrated in FIGS. 13 and 14. In still other implementations, a pair of stiffener loops 142 (and associated supports 196), with either the same or different dimensions as one another, may be employed adjacent to the base 120 and/or adjacent to the tip 118 in, for example, the manners described above with reference to FIGS. 17-20 and 26-30.

Another exemplary cochlear lead, which is generally represented by reference numeral 106h, is illustrated in FIGS. 45-49. The exemplary cochlear lead 106h is substantially similar to cochlear lead 106g and similar elements are represented by similar reference numerals. Here, however, a plurality of longitudinally spaced supports 202 are attached to the above-described stiffener loop 142 that is located the proximal region of the exemplary electrode array 108h. The supports 202 also augment the bending control aspect of the associated portion of the electrode array 108h, as compared to an otherwise identical electrode array without the supports, and may be formed from the same materials (and by the same methods) as the support 196. The stiffener loop 142 and supports 202 define a plane that may be parallel to the contact plane, or may be in other orientations, as is described above. In the illustrated implementation, the stiffener loop 142 and supports 196 are located within the handle tapered portion 130 and the portion of the flexible body 112 adjacent to be base 120. The exemplary supports 202 each include a main body 204 and a pair of grooves 206 in which portions of the stiffener loop side members 144 are located. The illustrated implementation also includes an end support 208 that is associated one of the curved end members (e.g., distal curved end member 148), while there is no end support associated with the other curved end member (e.g., proximal curved end member 146). The end support 208 includes a main body 210 and a U-shaped groove for the curved end member 148 of the stiffener loop 142 and adjacent portions of the side members 144. In other implementations, there may be an end support 208 associated with both of the stiffener loop curved end members 146 and 148, or neither of the stiffener loop curved end members.

The stiffener loop 142 and supports 202/208 may either be slightly offset from, or rest on, the associated contacts 114. The stiffener loop 142 and supports 202/208 may (as a group) in some instances be coextensive with the four contacts 114 that are adjacent to the base 120, i.e., the contacts thirteen to sixteen in the illustrated sixteen contact embodiment, in a manner similar to that illustrated in FIGS. 8 and 9. Alternatively, or in addition, a stiffener loop 142 and supports 202/208 may be located adjacent to the tip 118. Here, the stiffener loop 142 and supports 202/208 may in some instances be offset from, and coextensive with, the four contacts 114 that are adjacent to the tip 118, i.e., contacts one to four in the illustrated sixteen contact embodiment, in a manner similar to that illustrated in FIGS. 13 and 14. In still other implementations, a pair of stiffener loops 166 (and associated supports 202/208), with either the same or different dimensions as one another, may be employed adjacent to the base 120 and/or adjacent to the tip 118 in, for example, the manners described above with reference to FIGS. 17-20 and 26-30.

It should also be noted here that supports which are essentially the same as, or are similar to, the supports 196, 202 and 208 may be used in conjunction with any of the other stiffener loops described herein.

Another exemplary cochlear lead, which is generally represented by reference numeral 106i, is illustrated in FIGS. 50-53. The exemplary cochlear lead 106i is substantially similar to cochlear lead 106 and similar elements are represented by similar reference numerals. Here, however, the proximal region of the exemplary electrode array 108i includes a plurality of linked stiffener loops 214-1 to 214-4 (collectively "stiffener loops 214"), each with a pair of longitudinally extending side members 216, a proximal curved end member 218 and a distal curved end member 220. The stiffener loops 214, which are embedded in the flexible body 112, may be oriented such that the loop planes of two of the loops (e.g., loops 214-1 and 214-3) are parallel to the contact plane, or may be in other orientations, as is described above. In the illustrated implementation, the linked stiffener loops 214 are located within the handle tapered portion 130 and the portion of the flexible body 112 adjacent to be base 120. The linked stiffener loops 214 may either be slightly offset from, or may rest on, the associated contacts 114.

The linked stiffener loops 214 may in some instances be coextensive with the four contacts 114 that are adjacent to the base 120, i.e., the contacts thirteen to sixteen in the illustrated sixteen contact embodiment, in a manner similar to that illustrated in FIGS. 8 and 9. Alternatively, or in addition, the linked stiffener loops 214 may be located adjacent to the tip 118. Here, the stiffener loops 214 may in some instances be offset from, and coextensive with, the four contacts 114 that are adjacent to the tip 118, i.e., contacts one to four in the illustrated sixteen contact embodiment, in a manner similar to that illustrated in FIGS. 13 and 14. In still other implementations, two sets of linked stiffener loops 214, with either the same or different dimensions as one another, may be employed adjacent to the base 120 and/or adjacent to the tip 118 in, for example, the manners described above with reference to FIGS. 17-20 and 26-30. The number of linked stiffener loops may also be increased or decreased as desired.

Another exemplary cochlear lead, which is generally represented by reference numeral 106j, is illustrated in FIGS. 54-57. The exemplary cochlear lead 106j is substantially similar to cochlear lead 106 and similar elements are represented by similar reference numerals. Here, however, the proximal region of the exemplary electrode array 108j includes an undulating stiffener loop 222 with a pair of longitudinally extending undulating side members 224, a proximal curved end member 226 and a distal curved end member 228. The side members 224 undulate toward and away from one another. The stiffener loop 222, which is embedded in the flexible body 112, may be oriented such that the loop plane is parallel to the contact plane, or may be in other orientations, as is described above. In the illustrated implementation, the stiffener loop 222 is located within the handle tapered portion 130 and the portion of the flexible body 112 adjacent to be base 120. The stiffener loop 222 may either be slightly offset from, or rest on, the associated contacts 114.

The exemplary undulating stiffener loop 222 may in some instances be coextensive with the four contacts 114 that are adjacent to the base 120, i.e., the contacts thirteen to sixteen in the illustrated sixteen contact embodiment, in a manner similar to that illustrated in FIGS. 8 and 9. Alternatively, or in addition, a stiffener loop 222 may be located adjacent to the tip 118. Here, the stiffener loop 222 may in some instances be offset from, and coextensive with, the four contacts 114 that are adjacent to the tip 118, i.e., contacts one to four in the illustrated sixteen contact embodiment, in a manner similar to that illustrated in FIGS. 13 and 14. In still other implementations, a pair of undulating stiffener loops 220, with either the same or different dimensions as one another, may be employed adjacent to the base 120 and/or adjacent to the tip 118 in, for example, the manners described above with reference to FIGS. 17-20 and 26-30.

Figure 55:
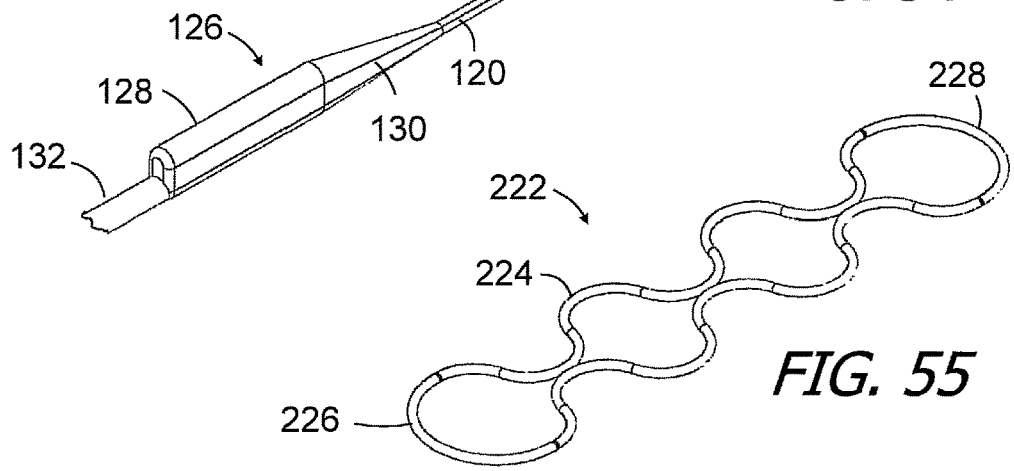
FIG. 55 is a perspective view of the stiffener of the cochlear lead illustrated in FIG. 54.
Figure 56:
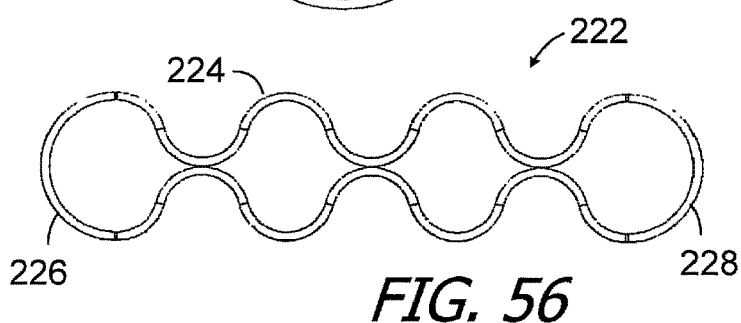
FIG. 56 is a top view of the stiffener illustrated in FIG. 55.
Figure 57:
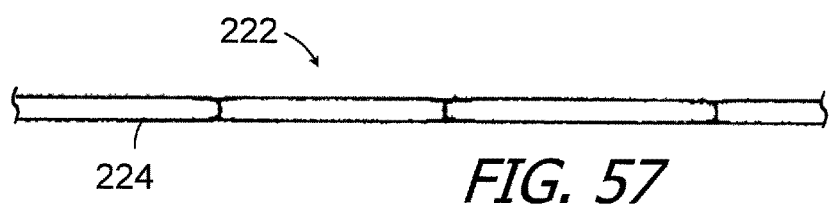
FIG. 57 is a side view of the stiffener illustrated in FIG. 55.
Figure 57A:
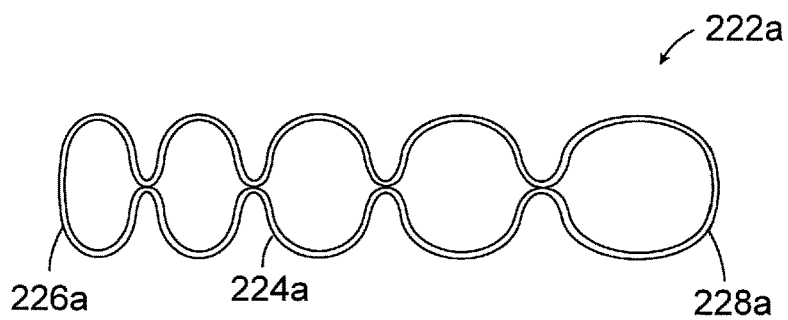
FIG. 57A is a top view of a stiffener in accordance with one embodiment of a present invention.
Figure 58:
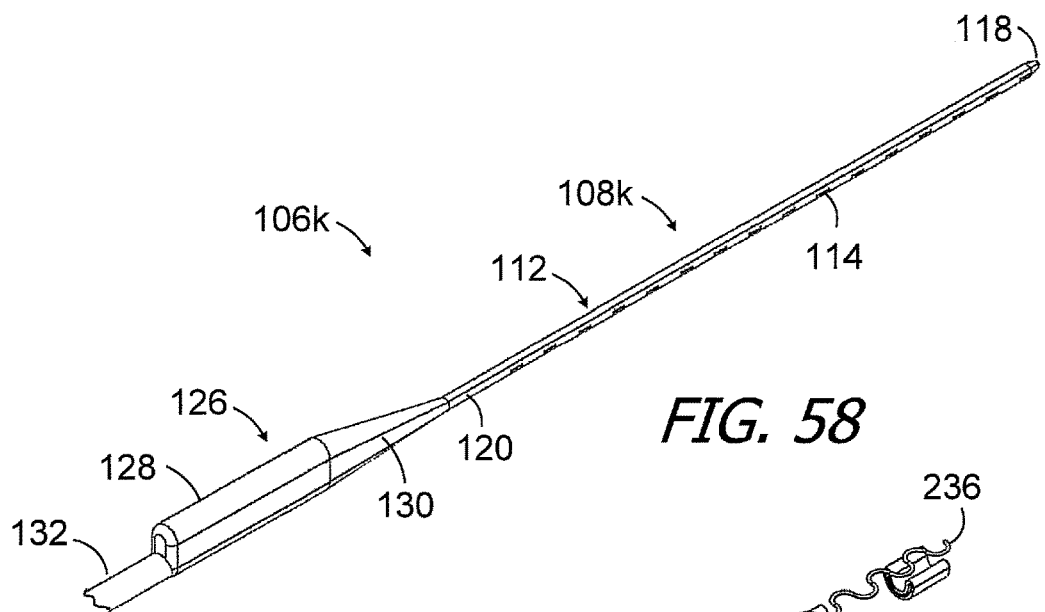
FIG. 58 is a perspective view of a portion of a cochlear lead in accordance with one embodiment of a present invention.
Figure 59:
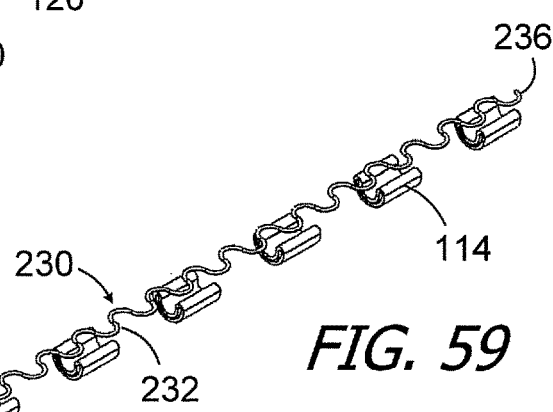
FIG. 59 is a perspective view of a portion of the cochlear lead illustrated in FIG. 58.
Figure 60:
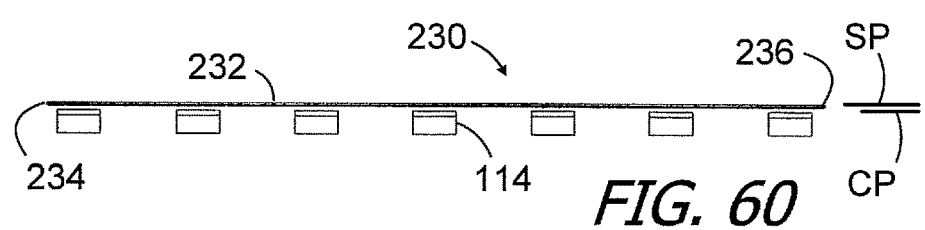
FIG. 60 is a side view of the portion of the cochlear lead illustrated in FIG. 59.

Undulating stiffener loops similar to that illustrated in FIGS. 55-57 may also be configured in such a manner that the stiffness is not constant along the length of the stiffener loop. Referring to FIG. 57A, the stiffness of the exemplary undulating stiffener loop 222a, which includes a pair of longitudinally extending undulating side members 224a, a proximal curved end member 226a and a distal curved end member 228a, decreases from the proximal (or "basal") region to the distal (or "apical") region. In particular, the peak to peak distance between the undulations increases from the proximal undulation to the distal undulation in the stiffener loop 222a, while the peak to peak distance between the undulations is constant in the stiffener loop 222 (FIGS. 55-57).

Another exemplary cochlear lead, which is generally represented by reference numeral 106k, is illustrated in FIGS. 58-62. The exemplary cochlear lead 106k is substantially similar to cochlear lead 106 and similar elements are represented by similar reference numerals. Here, however, the cochlear lead includes an undulating stiffener 230 that is embedded in the flexible body 112. The stiffener plane SP (i.e., the plane that extends longitudinally through the stiffener) may be parallel to the contact plane CP (as shown), or may be in other plane orientations, as is described above. The stiffener 230 may have a sinusoidal shape or other wave-like shape which cycles back and forth to define a width between peaks 232. The undulating stiffener 230, which also includes proximal and distal ends 234 and 236, is located within the handle tapered portion 130 and the portion of the flexible body 112 adjacent to be base 120. The undulating stiffener 230 may either be slightly offset from, or rest on, the associated contacts 114.

The exemplary undulating stiffener 230 may in some instances be coextensive with the seven contacts 114 that are adjacent to the base 120, i.e., the contacts ten to sixteen in the illustrated sixteen contact embodiment. In other instances, a shorter undulating stiffener 230 may be coextensive with the four contacts that are adjacent to the base 120 in a manner similar to that illustrated in FIGS. 8 and 9. Alternatively, or in addition, an undulating stiffener 230 may be located adjacent to the tip 118. Here, the undulating stiffener 230 may in some instances be offset from, and coextensive with, the four contacts 114 that are adjacent to the tip 118, i.e., contacts one to four in the illustrated sixteen contact embodiment, in a manner similar to that illustrated in FIGS. 13 and 14. In still other implementations, a pair of undulating stiffener loops 230, with either the same or different dimensions as one another, may be employed adjacent to the base 120 and/or adjacent to the tip 118 in, for example, the manners described above with reference to FIGS. 17-20 and 26-30.

Figure 61:
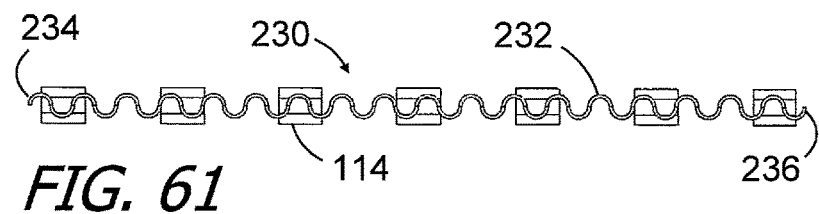
FIG. 61 is a top view of the portion of the cochlear lead illustrated in FIG. 59.
Figure 62:
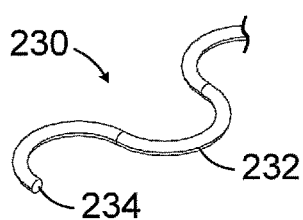
FIG. 62 is a perspective view of a portion of the stiffener of the cochlear lead illustrated in FIG. 58.
Figure 63:
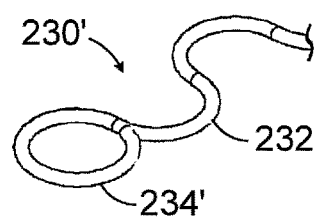
FIG. 63 is a perspective view of a portion of a stiffener in accordance with one embodiment of a present invention.
Figure 64:
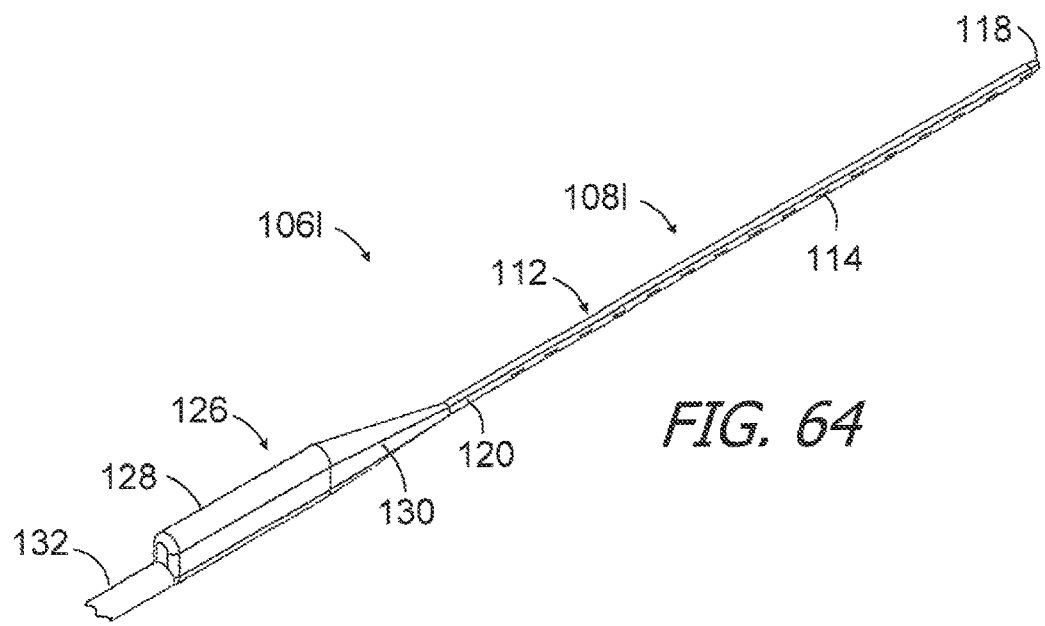
FIG. 64 is a perspective view of a portion of a cochlear lead in accordance with one embodiment of a present invention.
Figure 65:
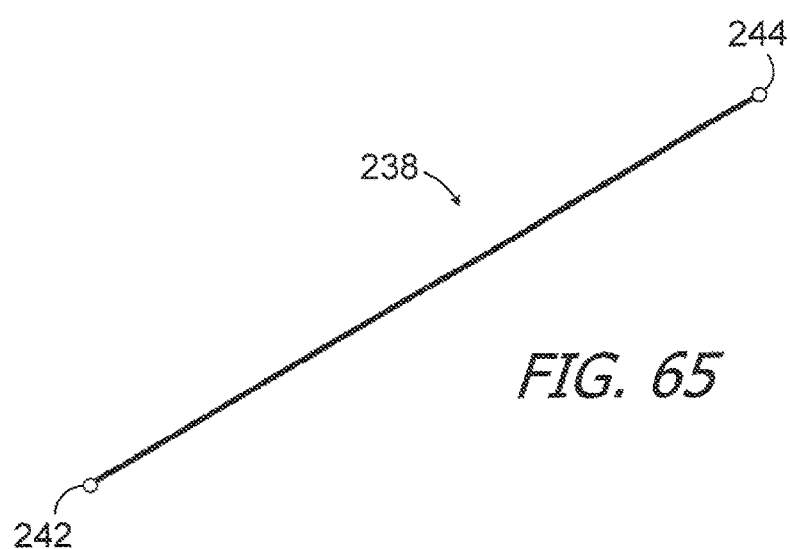
FIG. 65 is a perspective view the stiffener of the cochlear lead illustrated in FIG. 64.
Figure 66:
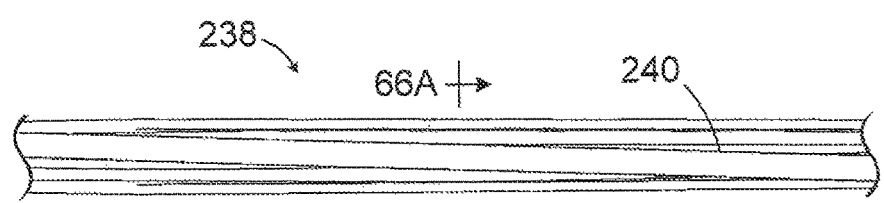
FIG. 66 is a side view of a portion of the stiffener illustrated in FIG. 65.
Figure 66A:
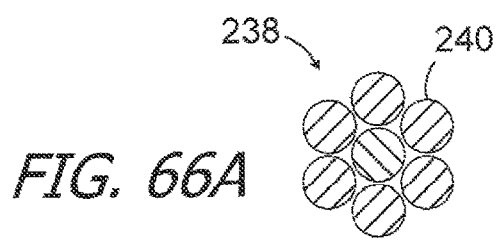
FIG. 66A is a section view taken along line 66A-66A in FIG. 66.

The respective configurations of the proximal and distal ends 234 and 236 may be adjusted as desired. Referring more specifically to FIGS. 61 and 62, the proximal and distal ends 234 and 236 may simply be the point at which the drawn filled tubing (or other material used to form the undulating stiffener 230) is terminated. The proximal and distal ends 234 and 236 also point in a direction that is transverse to the longitudinal direction to reduce the likelihood that the ends will tear through the electrode. Alternatively, to further reduce the likelihood of tearing, proximal end 234' may have a loop shape (FIG. 63), as may the distal end (not shown).

Undulating stiffeners similar to those illustrated in FIGS. 59-63 may also be configured in such a manner that the stiffness is not constant along the length of the stiffener loop. For example, the peak to peak distance between the undulations may increase from the proximal undulation to the distal undulation so that the stiffness of the undulating stiffener decreases from proximal undulation to the distal undulation.

Another exemplary cochlear lead, which is generally represented by reference numeral 106l, is illustrated in FIGS. 64-66A. The exemplary cochlear lead 106l is substantially similar to cochlear lead 106 and similar elements are represented by similar reference numerals. Here, however, the electrode array 108l includes a multi-strand stiffener 238 that is embedded in the flexible body 112. The multi-strand stiffener 238 may be parallel to the contact plane, or may be in other orientations, as is described above. The multi-strand stiffener 238 includes a plurality of individual strands 240 (i.e., two or more stands) that are wound into a rope-like state. In those instances where three or more strands are employed, one of the strands may function as a core around which the other strands are wound. By way of example, the multi-strand stiffener 238 includes a core strand 240 and six other strands wound around the core strand. The multi-strand stiffener 238, which includes proximal and distal ends 242 and 244, is located within the handle tapered portion 130 and the portion of the flexible body 112 adjacent to be base 120. The proximal and distal ends 242 and 244 may in some instanced be balled (as shown) by laser welding or flaming to reduce sharpness. Heat pressing (with flattened or swaged ends), tied ends, and other suitable techniques to reduce sharpness may also be employed. The multi-strand stiffener 238 may either be slightly offset from, or be in the contact plane of, the associated contacts 114.

The exemplary multi-strand stiffener 238 may in some instances be coextensive with the four contacts 114 that are adjacent to the base 120, i.e., the contacts thirteen to sixteen in the illustrated sixteen contact embodiment in a manner similar to that illustrated in FIGS. 8 and 9. Alternatively, or in addition, a multi-strand stiffener 238 may be located adjacent to the tip 118. Here, the multi-strand stiffener 238 may in some instances be offset from, and coextensive with, the four contacts 114 that are adjacent to the tip 118, i.e., contacts one to four in the illustrated sixteen contact embodiment, in a manner similar to that illustrated in FIGS. 13 and 14. In still other implementations, a plurality of multi-strand stiffeners 238, with either the same or different dimensions as one another, may be employed adjacent to the base 120 and/or adjacent to the tip 118.

Figure 67:
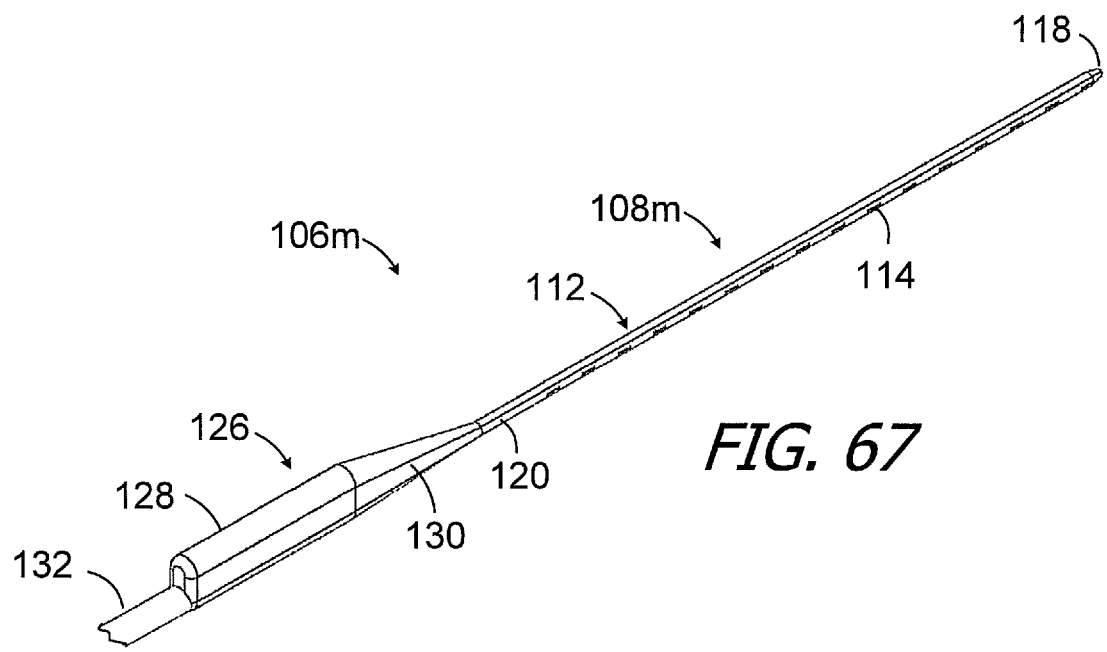
FIG. 67 is a perspective view of a portion of a cochlear lead in accordance with one embodiment of a present invention.
Figure 68:
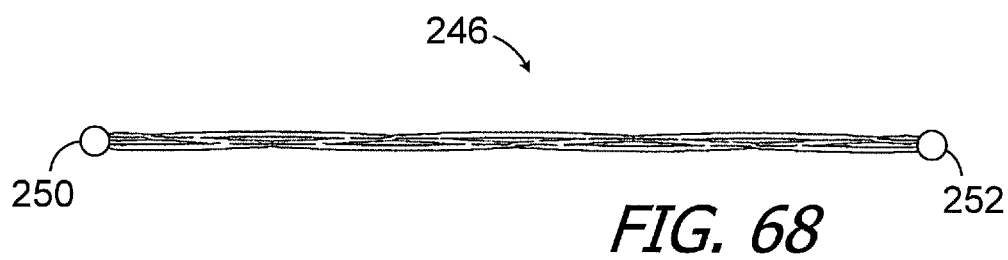
FIG. 68 is a top view the stiffener of the cochlear lead illustrated in FIG. 67.
Figure 69:
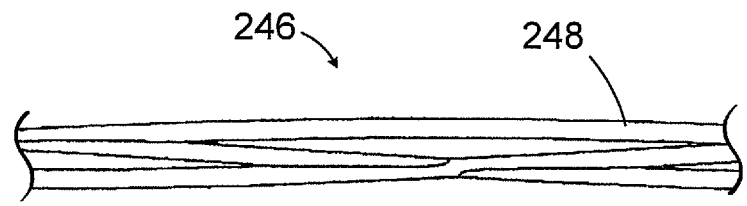
FIG. 69 is a top view of a portion of the stiffener illustrated in FIG. 68.

Another exemplary cochlear lead, which is generally represented by reference numeral 106m, is illustrated in FIGS. 67-69. The exemplary cochlear lead 106m is substantially similar to cochlear lead 106l and similar elements are represented by similar reference numerals. For example, the electrode array 108m includes a multi-strand stiffener that is embedded in the flexible body 112. Here, however, multi-strand stiffener 246 includes a plurality of individual strands 248 that are woven into a flat braid. The multi-strand stiffener 246 may be parallel to the contact plane, or may be in other plane orientations, as is described above. The multi-strand stiffener 238, which includes proximal and distal ends 250 and 252, is located within the handle tapered portion 130 and the portion of the flexible body 112 adjacent to be base 120. The proximal and distal ends 250 and 252 may in some instanced be balled (as shown) by laser welding or flaming to reduce sharpness. Heat pressing (with flattened or swaged ends), tied ends, and other suitable techniques to reduce sharpness may also be employed. The multi-strand stiffener 246 may either be slightly offset from, or may rest on, the associated contacts 114.

The exemplary multi-strand stiffener 246 may in some instances be coextensive with the four contacts 114 that are adjacent to the base 120, i.e., the contacts thirteen to sixteen in the illustrated sixteen contact embodiment in a manner similar to that illustrated in FIGS. 8 and 9. Alternatively, or in addition, a multi-strand stiffener 246 may be located adjacent to the tip 118. Here, the multi-strand stiffener 246 may in some instances be offset from, and coextensive with, the four contacts 114 that are adjacent to the tip 118, i.e., contacts one to four in the illustrated sixteen contact embodiment, in a manner similar to that illustrated in FIGS. 13 and 14. In still other implementations, a plurality of multi-strand stiffeners 246, with either the same or different dimensions as one another, may be employed adjacent to the base 120 and/or adjacent to the tip 118.

With respect to materials, the strands of the present multi-strand stiffeners (including strands 240 and 248 of the rope-like and flat braid stiffeners 238 and 246 described above with reference to FIGS. 64-69) may be formed from the above-described drawn filled tubing as well as biocompatible polymer microfibers (such as polyethylene and polypropylene microfibers), biocompatible metallic fine wire (such as platinum, platinum-iridium, and titanium fine wire), glass fibers, carbon nanotubes or other suitable materials. With respect to dimensions, the dimensions of the stiffeners (in directions perpendicular to the longitudinal axis of the cochlear lead) may range from about 0.1 mm to about 0.4 mm. For example, the diameter of a rope-like braid 238 in some instances may range from about 0.1 mm to about 0.4 mm, while in some instances the width of a flat braid 246 may be up to about 0.4 mm and the thickness may be as small as the diameter of the strands and as large as about 0.1 mm. As used herein, the term "about" means +/−10%. The diameter of the strands themselves will depend, at the low end, on the strand material and, at the high end, on the intended properties (e.g., stiffness and size) of the associated stiffener. By way of example, but not limitation, biocompatible polymer microfibers are available in diameters as low as 0.075 mm, biocompatible metallic fine wires are available in diameters as low as 0.010 mm, and glass fibers are available in diameters as low as 0.005 mm.

Some multi-strand stiffeners may include strands that are identical to one another, while other multi-strand stiffeners may include one or more stands that are different in material and/or size than the other strands. By way of example, but not limitation, a rope-like multistrand braid may include a biocompatible metallic fine wire core and a plurality of biocompatible polymer microfibers wound around the core, or may include a biocompatible polymer microfiber core and a plurality of biocompatible metallic fine wires wound around the core. Glass fibers and other suitable materials may also be used as the core or the strands wound around the core in other implementations. The core may be the same diameter as the other strands, or may be of a difference diameter.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. For example, any two of the above-described stiffeners may be employed in a single electrode array, with one stiffener adjacent to the base 120 and the other stiffener adjacent to the tip 118. It is intended that the scope of the present inventions extend to all such modifications and/or additions and that the scope of the present inventions is limited solely by the claims set forth below.

We claim:

1. A cochlear implant, comprising:
a housing;
an antenna within the housing;
a stimulation processor within the housing operably connected to the antenna; and
an electrode array, operably connected to the stimulation processor, including a flexible body defining a longitudinal axis, a proximal region and a distal region, a plurality of electrically conductive contacts on the flexible body, and at least one undulating stiffener that is within the flexible body, that undulates toward and away from the electrode array within a portion of the flexible body that is coextensive with at least some of the electrically conductive contacts, and that is electrically isolated from the electrically conductive contacts.

2. A cochlear implant as claimed in claim 1, wherein
the electrically conductive contacts define a contact plane; and
the at least one undulating stiffener defines a plane that is parallel to the contact plane.

3. A cochlear implant as claimed in claim 1, wherein
the electrode array includes a handle associated with the proximal region of the flexible body.

4. A cochlear implant as claimed in claim 3, wherein
the at least one undulating stiffener includes a portion within the handle and a portion within the proximal region of the flexible body.

5. A cochlear implant as claimed in claim 1, wherein
the at least one undulating stiffener undulates within a portion of the flexible body that is coextensive with four of the electrically conductive contacts.

6. A cochlear implant, comprising:
a housing;
an antenna within the housing;
a stimulation processor within the housing operably connected to the antenna; and
an electrode array, operably connected to the stimulation processor, including a flexible body defining a longitudinal axis, a proximal region and a distal region, a plurality of electrically conductive contacts on the flexible body, and at least one undulating stiffener that is within the flexible body, that includes longitudinally extending side members that undulate toward and away from one another, that undulates within a portion of the flexible body that is coextensive with at least some of the electrically conductive contacts, and that is electrically isolated from the electrically conductive contacts.

7. A cochlear implant as claimed in claim 6, wherein
the electrically conductive contacts define a contact plane; and
the at least one undulating stiffener defines a plane that is parallel to the contact plane.

8. A cochlear implant as claimed in claim 6, wherein the electrode array includes a handle associated with the proximal region of the flexible body.

9. A cochlear implant as claimed in claim 8, wherein the at least one undulating stiffener includes a portion within the handle and a portion within the proximal region of the flexible body.

10. A cochlear implant, comprising:
a housing;
an antenna within the housing;
a stimulation processor within the housing operably connected to the antenna; and
an electrode array, operably connected to the stimulation processor, including a flexible body defining a longitudinal axis, a proximal region and a distal region, a plurality of electrically conductive contacts on the flexible body, and an undulating stiffener loop within the flexible body and electrically isolated from the electrically conductive contacts.

11. A cochlear implant as claimed in claim 10, wherein the undulating stiffener loop undulates toward and away from the electrode array.

12. A cochlear implant as claimed in claim 10, wherein the undulating stiffener loop includes longitudinally extending side members that undulate toward and away from one another.

13. A cochlear implant as claimed in claim 12, wherein the undulating stiffener loop defines a length and a stiffness that is not constant over the length.

14. A cochlear implant, comprising:
a housing;
an antenna within the housing;
a stimulation processor within the housing operably connected to the antenna; and
an electrode array, operably connected to the stimulation processor, including a flexible body defining a longitudinal axis, a proximal region and a distal region, a plurality of electrically conductive contacts on the flexible body that define a contact plane, and at least one undulating stiffener within the flexible body that defines a plane that is parallel to the contact plane and is electrically isolated from the electrically conductive contacts, the undulating stiffener including longitudinally extending side members that undulate toward and away from one another and an alternating series of first bends that bend in a first direction and second bends that bend in a second direction that is opposite the first direction.

15. A cochlear implant as claimed in claim 14, wherein the electrode array includes a handle associated with the proximal region of the flexible body.

16. A cochlear implant as claimed in claim 15, wherein the at least one undulating stiffener includes a portion within the handle and a portion within the proximal region of the flexible body.

\* \* \* \* \*